United States Patent
Tumialan

(10) Patent No.: US 9,681,862 B1
(45) Date of Patent: Jun. 20, 2017

(54) MEDIAL LATERAL RETRACTOR SYSTEM AND RELATED METHODS

(71) Applicant: Luis M. Tumialan, Paradise Valley, AZ (US)

(72) Inventor: Luis M. Tumialan, Paradise Valley, AZ (US)

(*) Notice: Subject to any disclaimer, the term of this patent is extended or adjusted under 35 U.S.C. 154(b) by 0 days.

(21) Appl. No.: 14/320,253

(22) Filed: Jun. 30, 2014

Related U.S. Application Data

(63) Continuation-in-part of application No. 13/756,505, filed on Jan. 31, 2013, now Pat. No. 8,764,757.

(60) Provisional application No. 61/592,839, filed on Jan. 31, 2012.

(51) Int. Cl.
A61B 1/32 (2006.01)
A61B 17/02 (2006.01)

(52) U.S. Cl.
CPC .................... A61B 17/0206 (2013.01)

(58) Field of Classification Search
CPC .................................. A61B 17/0206
USPC ............. 600/201, 210, 215, 219, 231, 232; 606/279, 90, 99, 105, 86 A, 264
See application file for complete search history.

(56) References Cited

U.S. PATENT DOCUMENTS

| 4,829,985 | A | * | 5/1989 | Couetil | A61B 17/0206 600/232 |
| 5,944,658 | A | * | 8/1999 | Koros | A61B 17/0206 600/231 |
| 6,214,004 | B1 | * | 4/2001 | Coker | A61B 17/7077 606/105 |
| 7,473,222 | B2 | | 1/2009 | Dewey et al. | |
| 8,137,284 | B2 | * | 3/2012 | Miles | A61B 1/32 600/554 |
| 8,974,381 | B1 | * | 3/2015 | Lovell | A61B 17/0206 600/215 |
| 2007/0100212 | A1 | * | 5/2007 | Pimenta | A61B 5/0488 600/210 |
| 2008/0114208 | A1 | * | 5/2008 | Hutton | A61B 17/02 600/201 |

(Continued)

OTHER PUBLICATIONS

"Mast Quadrant Medial Lateral Blades Procedural Solutions Technique" published at least as early as 2006 by Medtronic Sofamor Danek USA, Inc.

(Continued)

Primary Examiner — Pedro Philogene
Assistant Examiner — David C Comstock
(74) Attorney, Agent, or Firm — Adam R. Stephenson, Ltd.

(57) ABSTRACT

A medial lateral retractor system includes a first medial lateral retractor arm, a second medial lateral retractor arm movably coupled thereto, and a base member coupler coupled to one of the first medial lateral retractor arm and the second medial lateral retractor arm. The base member coupler is configured to couple to a base member to which a rostral refractor blade and caudal retractor blade are coupled. The first medial lateral retractor arm is configured to move relative to the second medial lateral retractor arm in a direction substantially perpendicular to a direction of movement of the rostral retractor blade relative to the caudal retractor blade when the base member coupler is coupled to the base member. In implementations the medial lateral retractor system further includes the base member, the rostral retractor blade and the caudal retractor blade, and the base member is coupled to the base member coupler.

15 Claims, 21 Drawing Sheets

(56) References Cited

U.S. PATENT DOCUMENTS

2010/0081885 A1* 4/2010 Wing ................ A61B 17/0206
600/215

OTHER PUBLICATIONS

"The Use of the Interfuse, an Innovative Modular Intervertebral Body Fusion Device as a Less Invasive Alternative to the Conventional Bilateral Lumbar Intervertebral Fusion Systems" published at least as early as 2009 by the Department of Neurological Surgery Washington University St. Louis.

* cited by examiner

MEDIAL LATERAL RETRACTOR SYSTEM AND RELATED METHODS

CROSS REFERENCE TO RELATED APPLICATIONS

This document is a continuation-in-part of U.S. patent application Ser. No. 13/756,505, entitled "MIS TLIF Surgical Systems and Related Methods" to Luis Tumialân which was filed on Jan. 31, 2013, (the '505 Application), which application claimed the benefit of the filing date of U.S. Provisional Patent Application Ser. No. 61/592,839, entitled "MS TLIF Systems and Related Methods" to Luis Tumialân which was filed on Jan. 31, 2012 (the '839 application), the disclosures of each of which are hereby incorporated entirely herein by reference.

BACKGROUND

1. Technical Field

Aspects of this document relate generally to devices used in surgical operations, such as spinal surgeries.

2. Background Art

Minimally Invasive Transforaminal Lumbar Interbody Fusion (MIS TLIF) surgeries have been carried out using various conventional techniques and using various conventional surgical systems. An example of a conventional surgical system and technique for performing MIS TLIF can be found in Appendix A of the '839 Application which was previously incorporated entirely herein by reference.

SUMMARY

Implementations of a medial lateral retractor system may include: a first medial lateral retractor arm; a second medial lateral retractor arm movably coupled to the first medial lateral retractor arm; and a base member coupler coupled to one of the first medial lateral retractor arm and the second medial lateral retractor arm and configured to couple to a base member to which a rostral refractor blade and caudal retractor blade are coupled; wherein the first medial lateral retractor arm is configured to move relative to the second medial lateral retractor arm in a direction that is substantially perpendicular to a direction of movement of the rostral retractor blade relative to the caudal retractor blade when the base member coupler is coupled to the base member.

Implementations of a medial lateral retractor system may include one, all, or any of the following:

The medial lateral retractor may further include the base member, the rostral retractor blade and the caudal retractor blade, and the base member may be coupled to the base member coupler.

The medial lateral retractor system may be substantially formed of a radiolucent material.

The first medial lateral retractor arm and second medial retractor arm each may include a plurality of finger members.

A lateral adjuster may be coupled between the base member coupler and one of the first medial lateral retractor arm and second medial lateral retractor arm, the lateral adjuster configured to jointly move the first medial lateral retractor arm and second medial lateral retractor arm in a direction substantially perpendicular to a direction of movement of the rostral refractor blade relative to the caudal retractor blade when the base member coupler is coupled to the base member.

The lateral adjuster may include a first member slidably engaging a second member and a releasable lock coupled to one of the first member and second member and configured to selectively prevent and allow sliding of the first member relative to the second member.

A refractor arm width adjuster may be coupled to one of the first medial lateral retractor arm and the second medial lateral retractor arm and configured to adjust a distance between the first medial lateral retractor arm and second medial lateral retractor arm along a direction substantially perpendicular to a direction of movement of the rostral retractor blade relative to the caudal retractor blade when the base member coupler is coupled to the base member.

A first interconnect section may be coupled to the first medial lateral retractor arm, a second interconnect section may be coupled to the second medial lateral retractor arm and slidably engaging the first interconnect section, and a releasable lock may be coupled to one of the first interconnect section and second interconnect section and configured to selectively prevent and allow sliding of the first interconnect section relative to the second interconnect section, and the refractor arm width adjuster may be configured to slide the first interconnect section relative to the second interconnect section.

A retractor arm rotation adjuster may be coupled to one of the first medial lateral retractor arm and the second medial lateral retractor arm and configured to rotate the first medial lateral retractor arm relative to the second medial lateral retractor arm in a plane that is substantially perpendicular to a plane of rotation of the rostral refractor blade relative to the caudal retractor blade when the base member is coupled to the base member.

The retractor arm rotation adjuster may be configured to rotate one of the first medial lateral retractor arm and second medial retractor arm about an axle.

The first medial lateral retractor arm and second medial lateral retractor arm may be coupled together only with elements that do not obstruct a downwards-looking field of view between the rostral retractor blade and caudal retractor blade.

The first medial lateral retractor arm and second medial lateral retractor arm may be coupled together with a u-shaped element.

The base member coupler may be coupled to the base member at a location only made available upon distancing the rostral retractor blade from the caudal retractor blade a predetermined amount.

Implementations of a medial lateral retractor system may include: a first medial lateral retractor arm; a second medial lateral retractor arm movably coupled to the first medial lateral retractor arm; a base member coupler coupled to one of the first medial lateral retractor arm and the second medial lateral retractor arm; a base member coupled to the base member coupler; a rostral refractor blade coupled to the base member; and a caudal retractor blade coupled to the base member; wherein the first medial lateral retractor arm is configured to move away from the second medial lateral retractor arm in a direction that is substantially perpendicular to a direction of movement of the rostral retractor blade away from the caudal retractor blade when the base member coupler is coupled to the base member.

Implementations of a medial lateral retractor system may include one, all, or any of the following:

The base member coupler may be coupled to the base member at a location only made available upon distancing the rostral retractor blade from the caudal retractor blade a predetermined amount.

Implementations of a method of using a medial lateral retractor system may include: movably coupling a first medial lateral retractor arm to a second medial lateral retractor arm; coupling a base member coupler to one of the first medial lateral retractor arm and the second medial lateral retractor arm; and coupling the base member coupler to a base member, to which a caudal refractor blade and rostral retractor blade are coupled, at a location made available only by distancing the caudal retractor blade from the rostral retractor blade a predetermined amount; wherein the first medial lateral retractor arm is configured to move away from the second medial lateral retractor arm in a direction that is substantially perpendicular to a direction of movement of the rostral retractor blade away from the caudal retractor blade when the base member coupler is coupled to the base member.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

This disclosure, its aspects and implementations, are not limited to the specific components, assembly procedures or method elements disclosed herein. Many additional components, assembly procedures and/or method elements known in the art consistent with the intended MIS TLIF systems and related methods will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such MIS TLIF systems and related methods, and implementing components and methods, consistent with the intended operation and methods.

The '839 Application previously incorporated entirely by reference contains disclosure of a wide variety of instruments, assistive devices, interbody devices, and other components that can be utilized when performing MIS TLIF surgeries and will be referred to and in this document at various locations.

Figure 1:
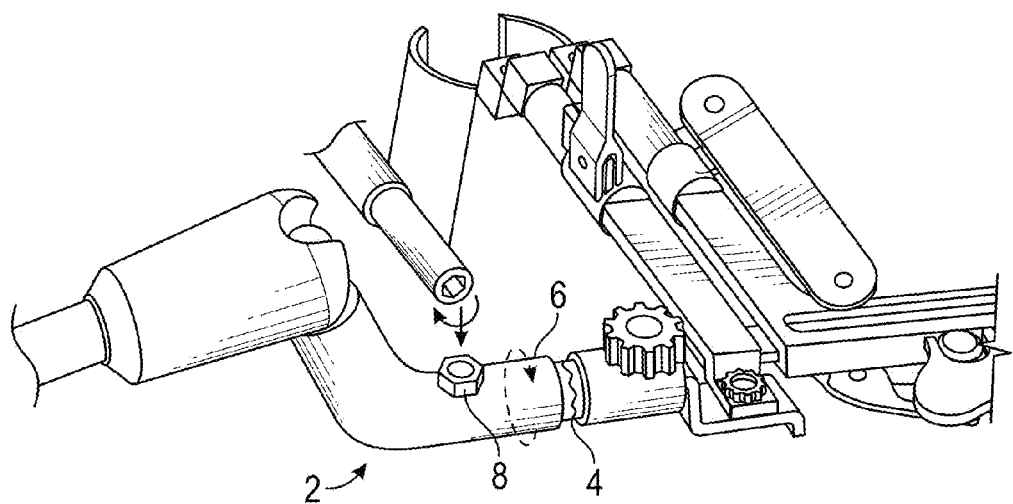
FIG. 1 is a perspective view of an implementation of a retractor arm with rotational capability.

Referring to FIG. 1, an implementation of a retractor arm 2 is disclosed. As illustrated, the retractor arm 2 contains an inserting portion 4 that is inserted into a sleeved portion 6. A set screw is biased against the inserting portion 4 through an opening in the sleeved portion 6 through rotation of nut 8. Implementations of retractor arms 2 that can be rotated through the sleeved portion allow the rotation of the arm 2 and fixing of it through the set screw at a desired angle. This rotational ability of retractor arm allows the surgeon to adjust the angle of the retractor relative to the vertebra over which the retractor is positioned during surgery. Adjustment of the angle may be desirable in a situation where the angle of the entry point for a pedicle screw into the pedicle is lateral to the neural elements and the angle needed for the retractor during decompression and placement of the interbody is medial. Being able to adjust the angle of the retractor to accommodate the pedicle screw insertion and the decompression without adjusting the overall position of the refractor arm can be very helpful, particularly when pedicle screw placement takes place first, followed by decompression and placement of the interbody, followed by placement of the rod, where the angle of the retractors must be adjusted first lateral to medial, then medial to lateral. While this mechanical ability of the retractor arm is useful in MIS TLIF surgeries, it can be used in other minimally invasive procedures as well, such as MIS lumbar laminectomies, where there is a need to angle the retractor medially for contralateral decompression and then angulate to an original neutral position for an ipsilateral decompression.

Figure 2:
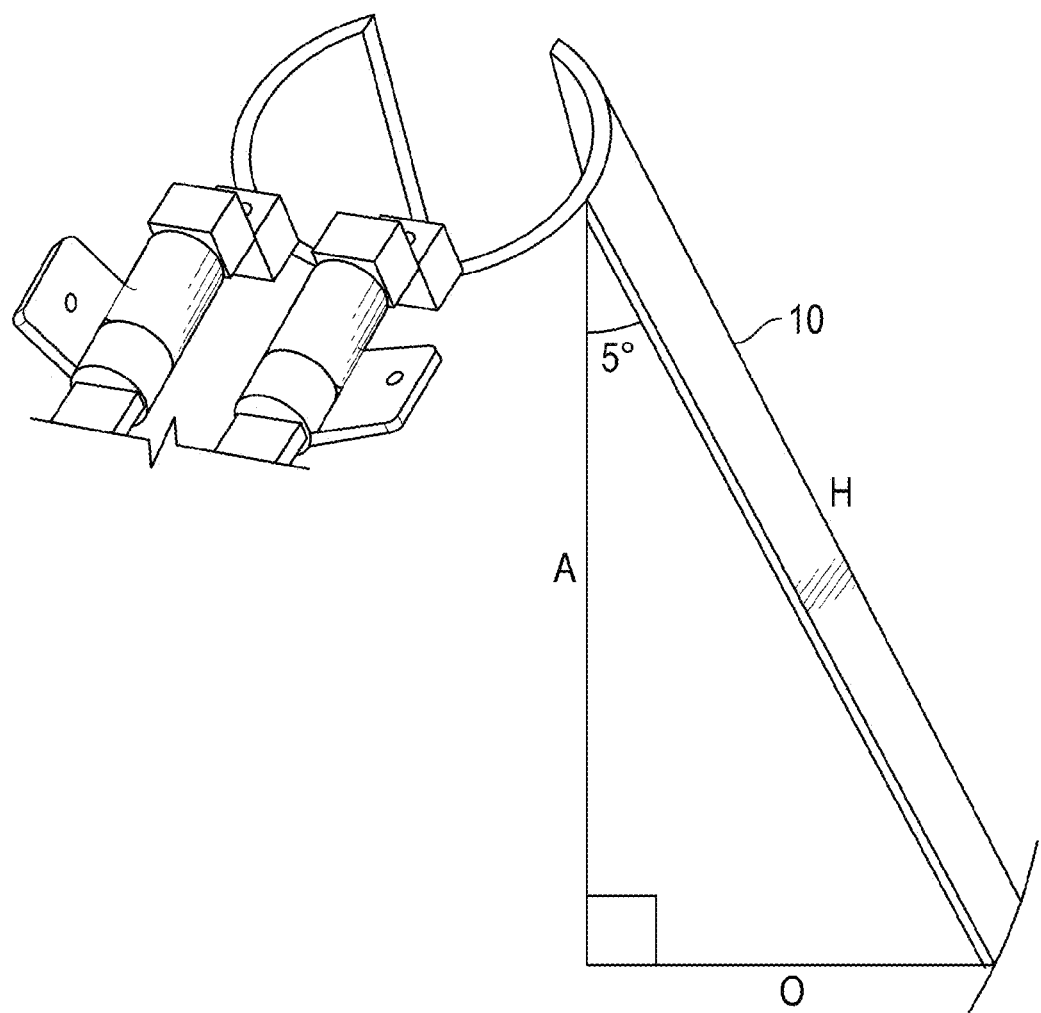
FIG. 2 is a cutaway view of a retractor blade.

During surgery, the blades associated with the retractor (retractor blades) that hold back the surrounding tissue and expose the vertebrae are often angled in the rostral and caudal directions following initial opening of the retractor. This is done to permit additional exposure at depth to allow the surgeon to work without widening the initial opening in the patient's back. At the point in time when the retractor is initially opened and the blades are not angled, the width of the blades is known through use of the measurement markings on the retractor. However, once the blades begin to be angled rostrally and caudally in either of the three present blade angles, the exposure at depth, or the exposure at the bottom of the blades, will be greater or less than the original exposure when the blades were originally not angled, depending on the angle of the blades. The width at depth can be calculated using trigonometry and the sine function with knowledge of the angle at which the particular blade is placed. For instance (and referring to the diagram illustrated in FIG. 2), a retractor opened to a width of 28 mm as determined by the graduated retractor with a 6 cm blade angled to the first angle mark on the rostral blade and with no angle on the caudal blade has an exposure value calculated as the sine of the angle of the blade times the length of the blade plus the total width of the retractor, which would be approximately 5 mm plus 28 mm or 33 mm. If the difference of the exposure and depth value and the exposure shown on the measurement marking were included on a chart for every blade from 4-8 cm and for every angle (there are currently three preset angles in various conventional retractor implementations), the surgeon could quickly ensure that the minimum needed exposure at depth is maintained throughout the surgery as angles on the blades are changed. The charted values of angle depths may then be added to the retractor width shown on the scale on the graduated retractor implementations disclosed in the '839 Application and the total exposure at depth is now known. FIG. 2 is a diagram of this calculation showing the angled blade 10 and the angle exposure value O.

The foregoing discussion indicates that as the blades are angled, the width of the exposure changes. The same geometry that drives the exposure change also indicates that the length of the blade in the perpendicular direction to the retractor arms also decreases as the blade is angled. Because as the blades are angled medially and caudally to increase the exposure at depth following the initial creation of exposure using the blades, the ends of the blades may no longer be directly adjacent the vertebrae as the result of the change in angle. This can be referred to as "creep" where the length of required exposure may exceed the length of the blade after the angling of the blades to the desired angle and exposure value has been accomplished. This situation results from the application of the same geometric principles discussed previously.

Figure 3:
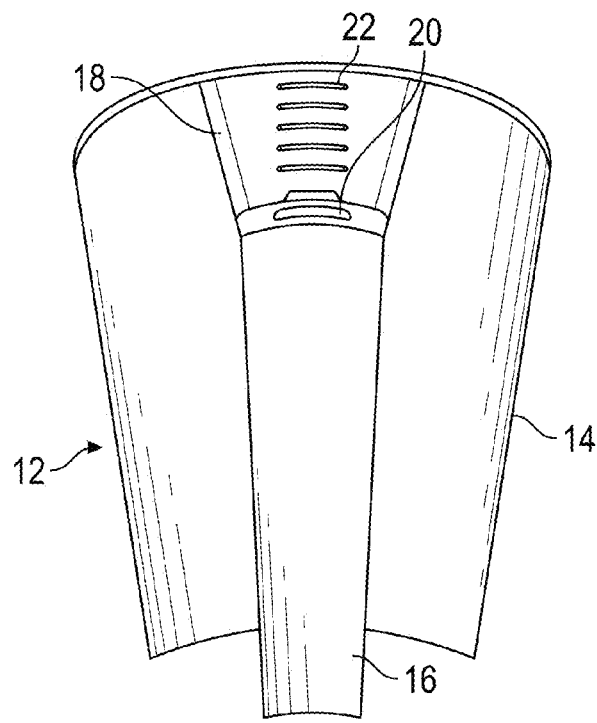
FIG. 3 is a perspective view of a retractor blade with a sleeved extender.

To counter the geometric loss in length of the blade due to medial and caudal angling, altering the structure of the blades to allow them to be lengthened during surgery would assist in eliminating the creep or increasing the exposure. Referring to FIG. 3, in one blade implementation 12, the blade 14 includes a sleeved extender 16 capable of slidably moving within a race 18 in the blade 14. During use, the surgeon would extend the extender 16 beyond the blade edge when increased exposure required the blade to be longer than the existing blade length. As illustrated, the extender 16 may have a groove 20 at one end that can receive an end of an adjuster designed to aid the surgeon in extending the extender at the desired length. One or more grooves 22 may be incorporated in the surface of the blade 14 that engage with a projection or lip extending from the sleeved extender to aid in ensuring the sleeved extender remains at the desired length. In some implementations, actual or scaled measurement markings may be utilized to inform the surgeon of the depth or length of the blade plus the extended portion of the sleeved extender.

In various implementations, the extender 16 may be extended using the same inserter that is used to extend the blades originally. In some implementations, the extender 16 may be automatically extended to a preset value as the blade is angled through use of a mechanical linkage between the retractor arm and the extender 16 that pushes the extender 16 downwardly and outwardly a preset amount as the blade 14 is rotated to a preset angle. In other implementations, the extender 16 may be automatically extended through use of a motor and gearing that is connected to a control circuit that senses the angle of the blade 14 and drives the extender 16 downwardly a corresponding distance to the angle of the blade 14.

Figure 4:
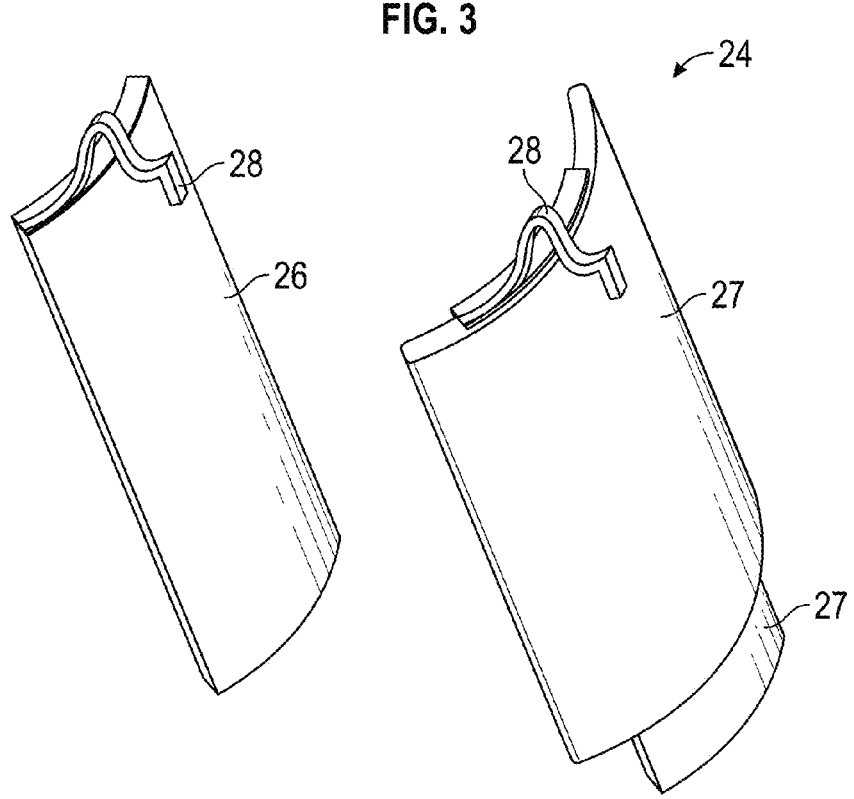
FIG. 4 is a perspective view of a cover slip sleeved extender implementation and a retractor blade.

Referring to FIG. 4, in another blade implementation 14, the length of the blade 24 could be extended through a cover-slip blade extender 26. In these implementations, the cover slip blade 26 would be narrower than the current blade 27 and would slide over the interior side of the blade 27 downwardly until held in place against the blade 27 using a clip 28. Various cover-slip blades of various preset lengths could be included that each correspond to a particular angle value of the retractor. During surgery, the surgeon would select the cover-slip blade needed for the particular retractor blade angle being used and remove it when the angle was changed.

Figure 5:
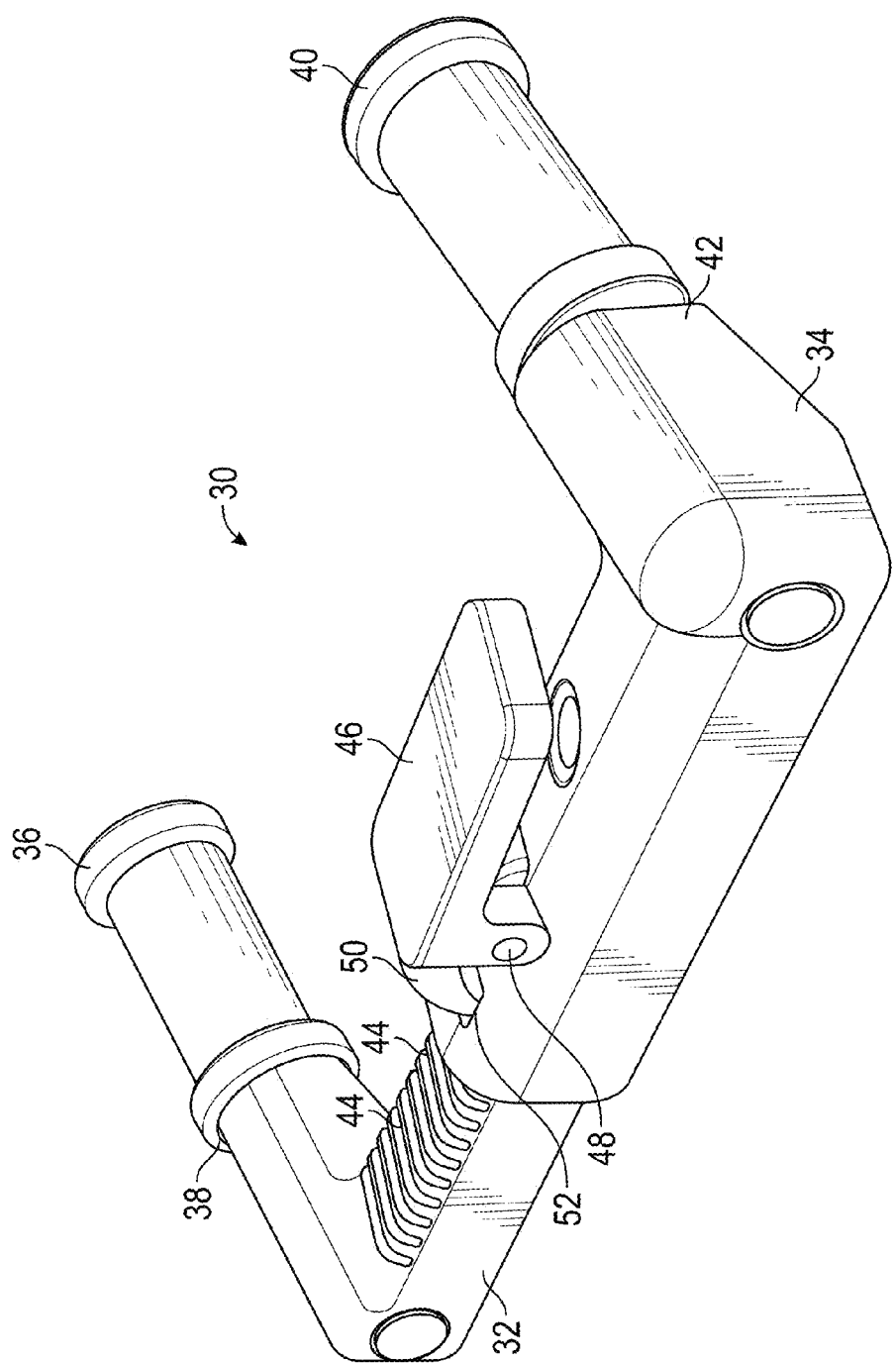
FIG. 5 is a perspective view of a first implementation of a distractor device.

Referring to FIG. 5, an implementation of a distractor device (distractor) 30 is illustrated. The distractor 30 includes a first portion 32 slidably coupled into a second portion 34. A first pedicle screw pin 36 is coupled to the end 38 of the first portion 32 and a second pedicle screw pin 40 is coupled to the end 42 of the second portion 34. The first portion 32 contains a plurality of teeth 44. A distractor latch 46 is coupled to the second portion 34 through a pin 48. In various implementations, the distractor latch 46 is biased using a spring. In various implementations, the distractor latch 46 has a projection 50 that extends through an opening 52 in the second portion 34 and contacts the plurality of teeth 44. The bias force from the spring may press the projection 50 downwardly into a space between two of the plurality of teeth 44. In various implementations, the first and second pedicle screw pins 36, 40 may be coupled to the ends 38, 42 of the first portion 32 and second portion 34, respectively through use of pins, welds, glues, or any other coupling mechanism or may be integrally formed with the first and second portions 32, 34, respectively. In various implementations, a distractor latch may not be used, but a mechanical tightener that operates to fix the one or both of the portions of the distractor together as the tightener is rotated may be utilized (similar to the structures employed with various length-adjusting rods, such as with pool cleaning equipment or tripod legs).

Figure 6:
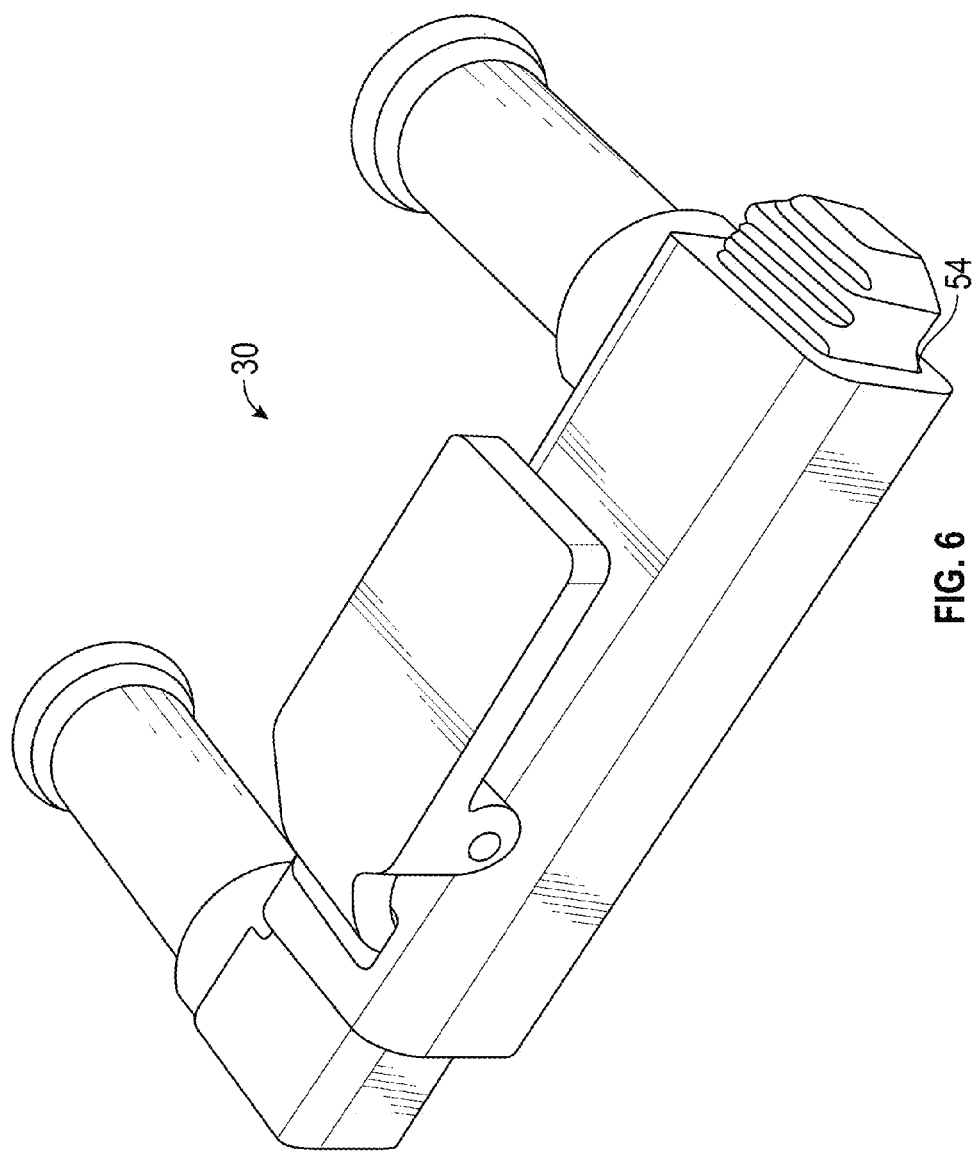
FIG. 6 is a perspective view of the implementation of the distractor device of FIG. 5 in a retracted position.

In various implementations, the first portion 32 may be a rod and the second portion 34 may be a sleeve that is sized to slidably couple over the rod. In various implementations, the first pedicle screw pin 36 and second pedicle screw pin 40 extend substantially parallel from a same side of the distractor (i.e., they both point the same direction from the same side of the distractor). The two pins 36, 40 also are at the same angle to a plane formed by the top flat surface of the distractor latch. This plane is substantially parallel with the second portion. Referring to FIG. 6, in various implementations, a length (longest dimension) of the distractor 30 is varied by slidably moving the sleeve over the rod. As illustrated, the sleeve may have an open end 54 that permits the end of the rod to extend through it when the distractor 30 is in a retracted position (the position the distractor is shown in FIG. 6. In this retracted position, the length of the distractor 30 may at its shortest value.

Figure 7:
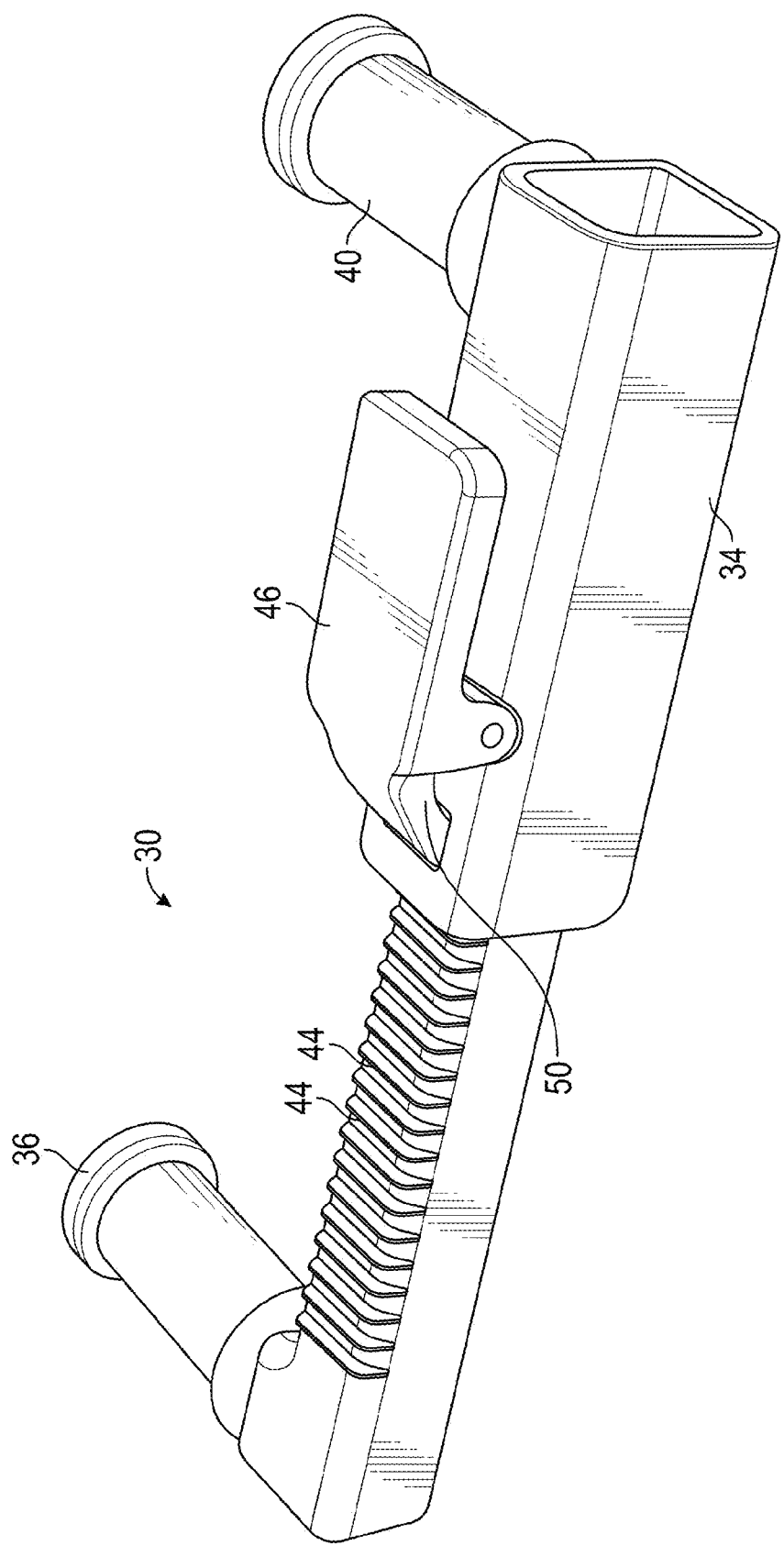
FIG. 7 is a perspective view of the implementation of the distractor device of FIG. 5 in an extended position.

Referring to FIG. 7, the distractor 30 is shown in an extended position. To transition from the retracted position to the extended position, the surgeon may press downward on the distractor latch 46, thereby disengaging the projection 50 from the plurality of teeth 44 and slide the second portion 34 so as to increase the length of the distractor. When the desired length is reached, the surgeon may let go of the distractor latch 46 and reengage the projection 50 with the plurality of teeth as the projection 50 moves downwardly under spring bias force. In various implementations, a spring may not be employed, and the projection 50 may be held in contact at a desired position through the plurality of teeth through gravity force and/or bias forces applied at the ends of the first and second pedicle screw pins 36, 40.

Figure 8:
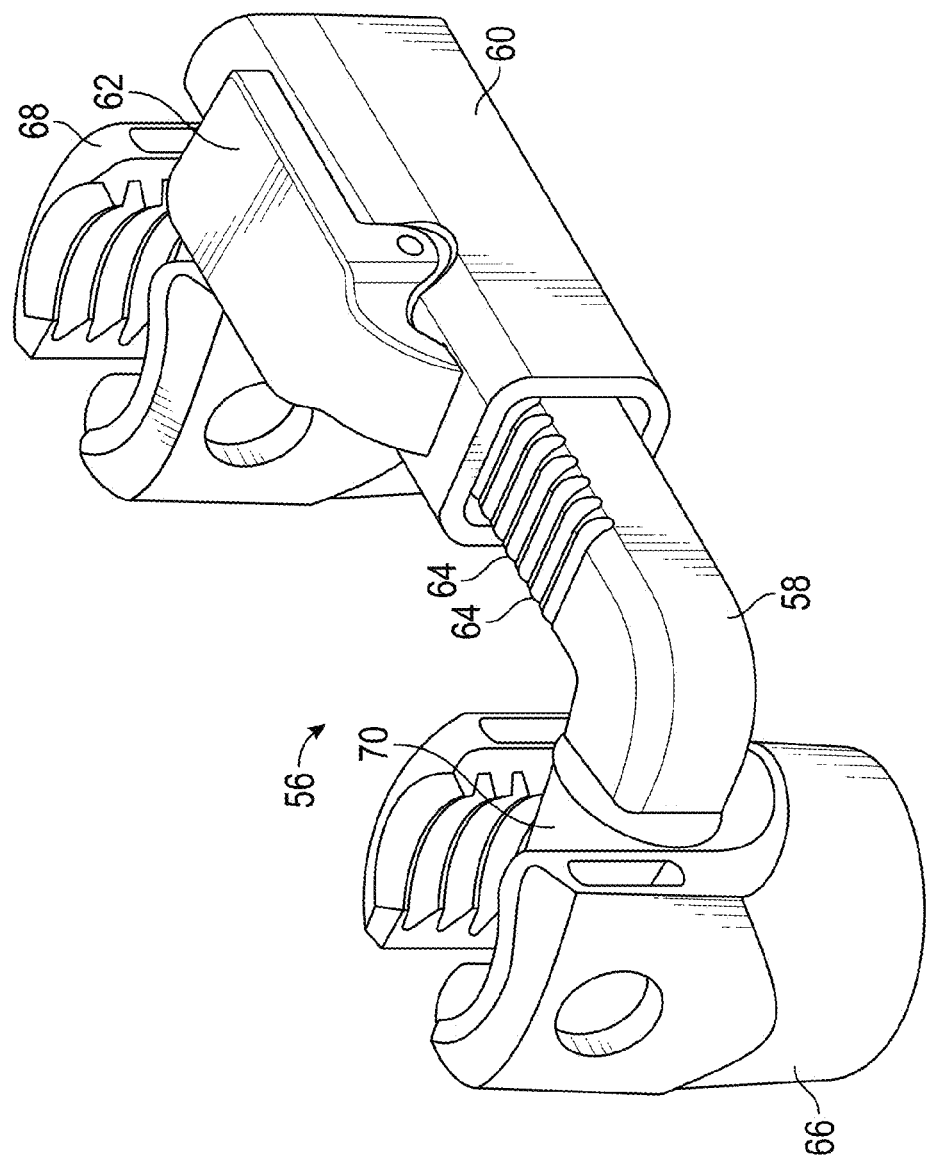
FIG. 8 is a perspective view of a second implementation of a distractor device coupled to two pedicle screw heads.

Referring to FIG. 8, a second implementation of a distractor 56 is illustrated. As illustrated, the distractor 56 includes a first portion 58 (rod) and a second portion 60 (sleeve), and a distractor latch 62 coupled with a plurality of teeth 64. Here, the distractor 56 is illustrated coupled with two pedicle screw heads 66, 68. In this implementation, the first pedicle screw pin 70 and the second pedicle screw pin 72 both extend from the end of the first portion 58 and the an end of the second portion 60 on the same side of the distractor device. Implementations of distractors disclosed herein are used to aid the surgeon in capturing height restoration between two vertebrae during an MIS TLIF operation. These distractors are used during the process of trialing and placing the graft and/or interbody device following discectomy. In an MIS TLIF operation, an ideal interbody device will restores the foraminal height and coronal balance between the two vertebrae. The surgeon typically strives to place the largest and widest graft/interbody device to ensure an optimal environment for fusion and restore the disc space to anatomical height. In certain circumstances, the advanced degeneration present in the patient results in severe disc collapse, which creates a challenging scenario for interbody preparation and graft placement, as the space between the two vertebrae is substantially reduced due to the existing anatomy. Conventionally, provisional rods have been used to hold open the disc space where the provisional rods are placed on the side contralateral to the TLIF. As the disc space is accessed, pedicle screws inserted into the vertebrae, and the height restored by the surgeon, a provisional rod is placed in the pedicle screws and set screws are secured into the heads of the pedicle screws over the provisional rod to hold it in place and capture the height restoration. Since the provisional rod that is placed is seldom the rod that would be ultimately implanted, the work of provisional rod placement and set screw placement is lost and the same task must be repeated when the definitive implanted rod is placed. Furthermore, as the height is restored, often the provisional rod that has been placed becomes too short and needs to be replaced with a longer one, which results in an iterative provisional rod placement process where rods of greater lengths must be inserted and secured with set screws.

The distractor device implementations disclosed herein couple with the pedicle screw heads without the need for use of set screws to couple with the pedicle screw pins. As illustrated in FIG. 8, the pedicle screw pins 70, 72 fit substantially perpendicularly into the set screw openings in the pedicle screw heads 66, 68. Once seated in the pedicle screw heads 66, 68, the distractor 56 permits the surgeon to use the distractor latch 62 to distract, or lengthen and/or shorten the space between the two vertebrae and slidably set the distance between the two vertebrae with the latch and the plurality of teeth 64. Because the length of the distractor 56 is adjustable through the plurality of teeth 64 and the distractor latch 62, the surgeon can adjust the length of the distractor 56 during surgery without having to remove the distractor 56 to do so from the pedicle screw heads 66, 68.

Figure 20:
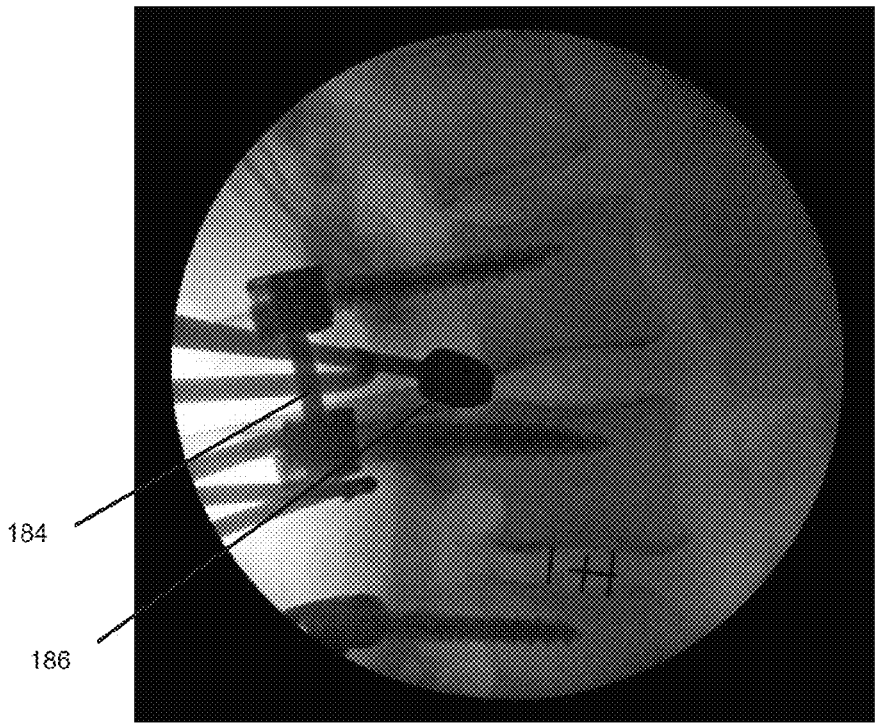
FIG. 20 is an intraoperative fluoroscopic image of a trial attempting to be inserted between two vertebrae.
Figure 21:
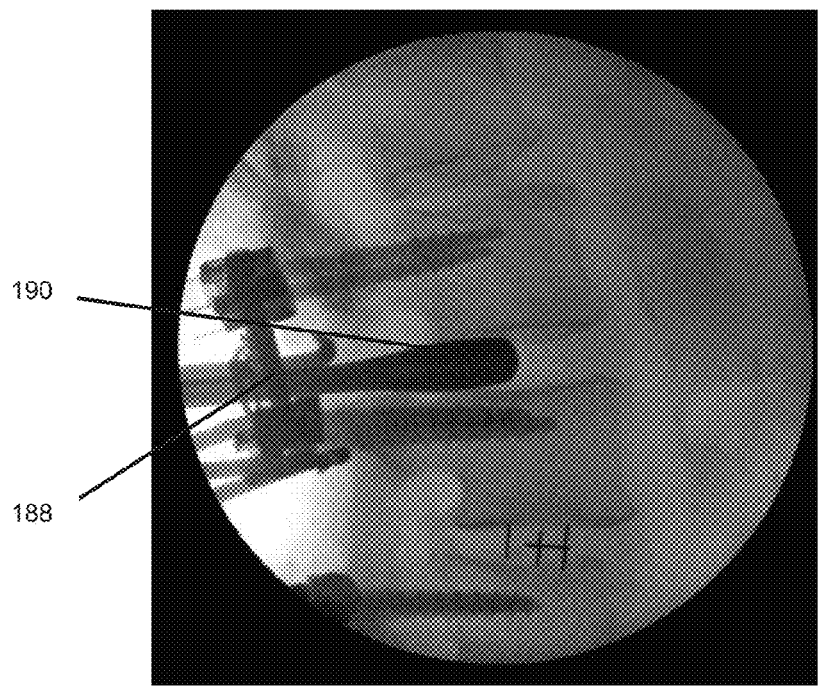
FIG. 21 is an intraoperative fluoroscopic image of a trial being inserted between two vertebrae after separation of the vertebrae using a distractor.
Figure 22:
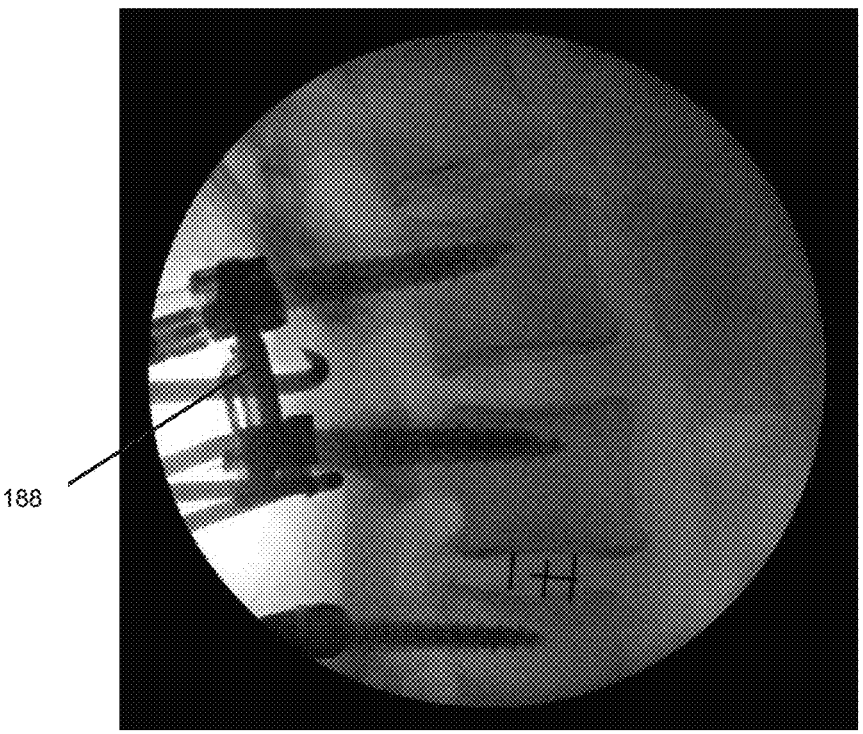
FIG. 22 is an intraoperative fluoroscopic image of the vertebrae after removal of the trial showing the distractor maintaining the space between the vertebrae.
Figure 23:
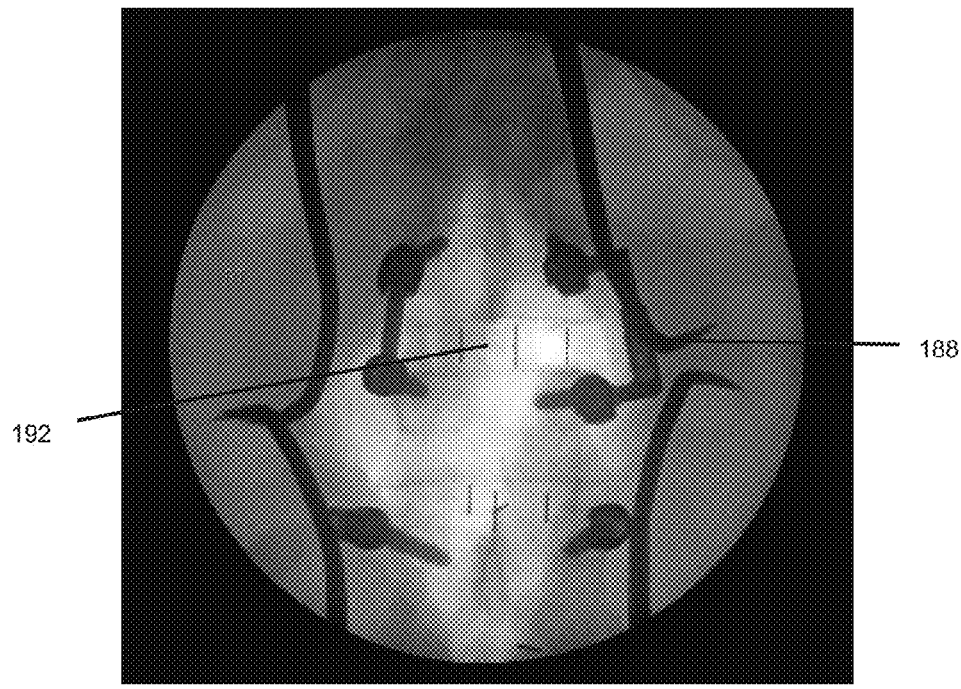
FIG. 23 is an intraoperative fluoroscopic image of the distractor in place after placement of the interbody devices on both levels in a two level MIS TLIF surgery.

Referring to FIG. 20, a lateral intraoperative fluoroscopic image is shown of a provisional rod 184 coupled to two pedicle screws. A trial 186 is also shown which is not able to be inserted between the two vertebrae because the space between the vertebrae has been reduced and is insufficient. Referring to FIG. 21, another lateral intraoperative fluoroscopic image, a distractor 188 is illustrated coupled to the two pedicle screws. The surgeon has used the distractor 188 to distract the two vertebrae, and a larger trial 190 than the trial 186 is now shown inserted between the two vertebrae. The distractor 188 has accordingly enabled the two vertebrae to be spread further apart and has improved the alignment of the two vertebrae relative to each other when compared with the provisional rod. FIG. 22 is a lateral intraoperative fluoroscopic image showing the same vertebrae and distractor 188 with the trial 190 removed. The width of the space between the vertebrae is now maintained solely by the distractor even without the trial 190 present. FIG. 23 is an anterior-posterior (AP) intraoperative fluoroscopic image of the vertebrae shown in FIGS. 20-22 showing the distractor 188 after placement of the second interbody spacer 192. This image demonstrates how the distractor's alignment ensures that the surgeon still has access to the disc space, when compared with the conventional rod on the opposite side of the vertebra.

When conventional provisional rods are used, the position of the rods is contralateral to the interbody access, which may cause the rod to have a limited ability to maintain the height on the side where the TLIF is performed. In these circumstances, it would be ideal for a provisional rod to be used on the side of the interbody access. There are some physical limitations in the capacity to do so in a minimally invasive approach, first because of an inability to place the caudal pedicle screw for pedicle screws systems with a larger pedicle screw profile. In these instances, the caudal pedicle screw is left out on the TLIF side, because it will interfere with access to the disc space. For example, in an L4-5 TLIF from the left, the left L5 pedicle screw is left out until the interbody placement is complete. However, where lower profile pedicle screw systems are employed, the left L5 pedicle screw may be placed with minimal interference for the discectomy and interbody preparation. The second physical limitation that exists with conventional provisional rods is the physical placement of the rod. Even with low profile pedicle screw systems, the placement of a straight rod will block access to the disc space in a minimally invasive approach. Because of this, attempting to use the provisional rod to capture distraction of the vertebrae may be untenable in various situations because the surgeon's access to the disc space is now compromised.

Implementations of distractors like those disclosed in this document may permit the surgeon to continue to have ongoing access to the disc place because the distractor is placed on the lateral side or side of the vertebrae opposite the midline. In these implementations, the distractor maintains the distraction of the vertebrae, but since the distractor is located on the lateral side of the pedicle screw heads, the distractor is not located over the disc space.

Figure 9:
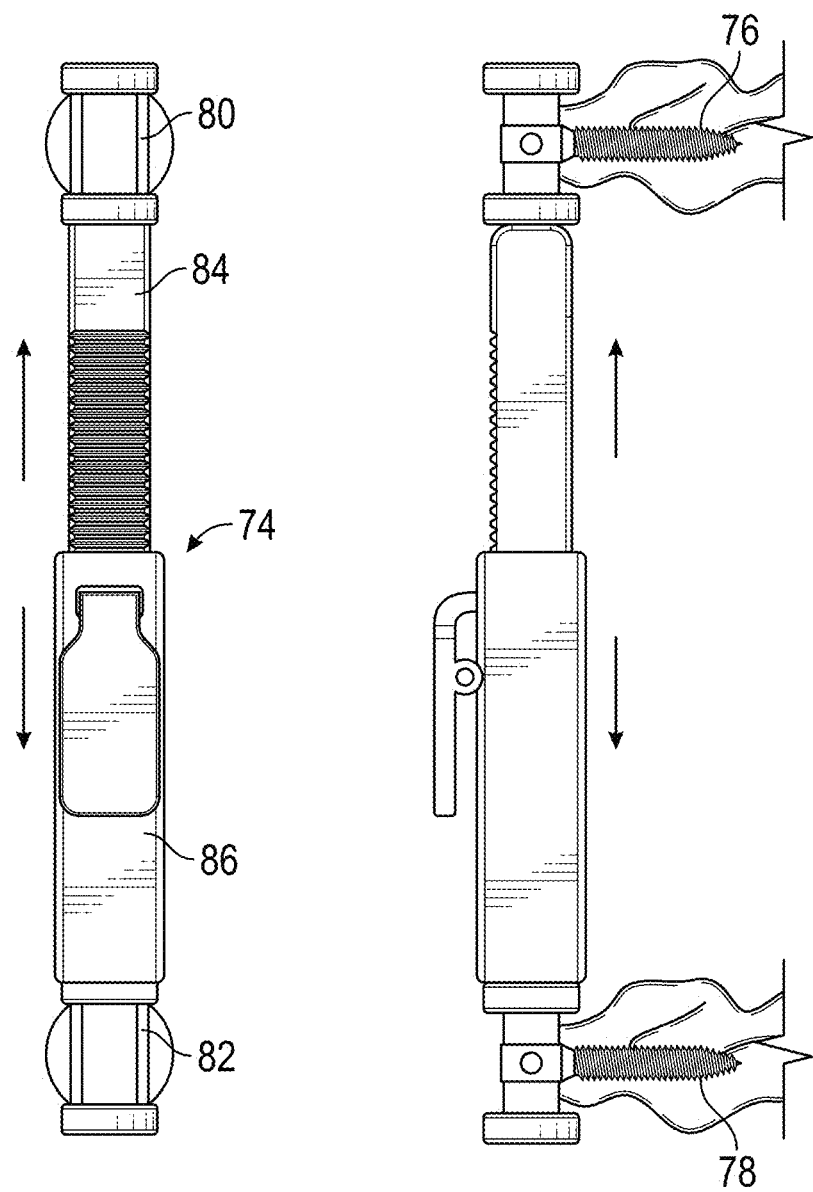
FIG. 9 is a top and side view of a third implementation of a distractor device.

Referring to FIG. 9, an implementation of a distractor 74 is illustrated. As illustrated by the arrows, the distractor 74 is capable of increasing or decreasing its length to accommodate a desired value of distraction between the two vertebrae to which it is coupled through the two pedicle screws 76, 78. In this implementation, the distractor 74 is straight and a line running through the longest dimension of the pedicle screw pins 80, 82 also runs through the rod 84 and sleeve 86 of the distractor 74. The overall shape of this distractor 74 is similar to a conventional provisional rod. Accordingly, this distractor 74 may allow the surgeon to adjust the distraction between the vertebrae, but may block access by the surgeon to the disc space in various situations.

Figure 10:
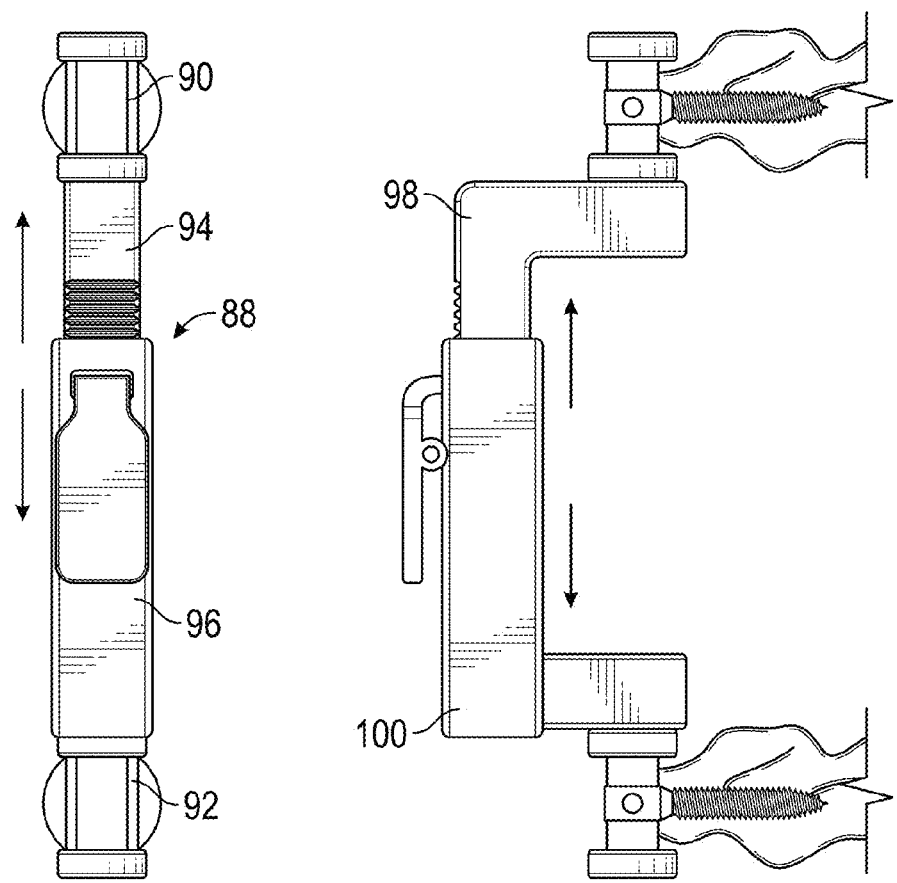
FIG. 10 is a top and side view of a fourth implementation of a distractor device.

Referring to FIG. 10, another implementation of a distractor 88 is illustrated. As illustrated, this distractor functions similarly to the implementation illustrated in FIG. 9. Viewed from the top view illustrated in the left most figure, the distractor 88 likewise is straight and a line running through the longest dimension of the pedicle screw pins 90, 92 also runs through the rod 94, and sleeve 96 of the distractor 88. In the distractor 74 illustrated in FIG. 9 and the distractor illustrated in FIG. 10, the first pedicle screw pins 80, 90 and second pedicle screw pins 82, 92 extend from the end of the rods 84, 94 and sleeves 86, 96 substantially parallel with the rods 84, 94, and the sleeves 86, 96, respectively. However, the rod 94 contains an elbow 98 and the sleeve 96 contains an elbow 100. As illustrated, due to the presence of the elbows 98, 100, rod 94 and the sleeve 96 are offset from the pedicle screw pins 90, 92. In this implementation, because the rod 94 and sleeve 96 are offset, depending upon the angle at which the distractor 88 is coupled into the pedicle screw pins 90, 92, the distractor 88 may not significantly block access by the surgeon to the disc space.

Figure 11:
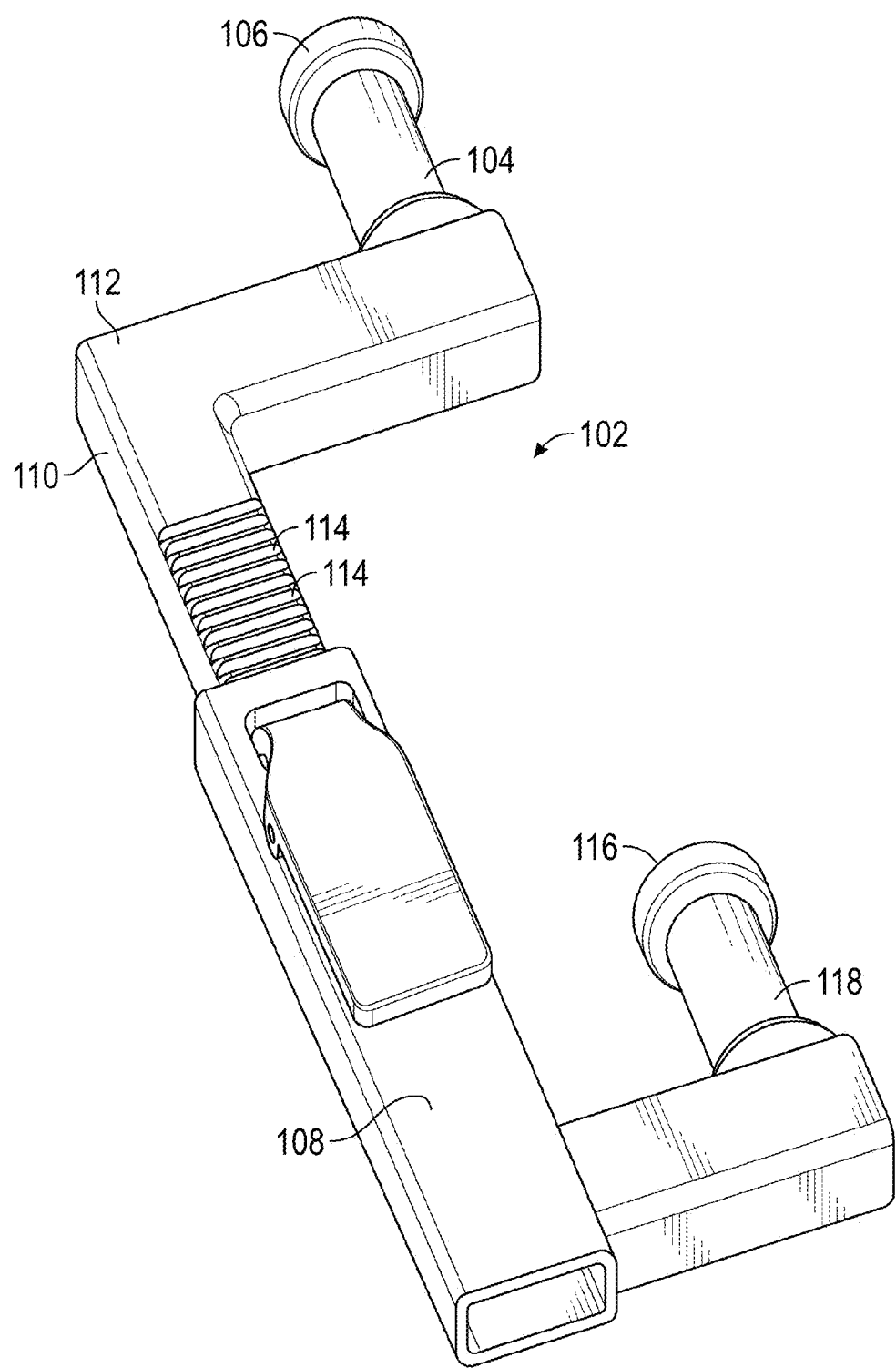
FIG. 11 is a perspective view of a fifth implementation of a distractor device.

Referring to FIG. 11, another implementation of a distractor 102 (J-shaped distractor) is illustrated. As illustrated, the distractor 102 includes a first pedicle screw pin 104 that has an end 106 that faces away from the second portion 108 and is aligned substantially parallel with the portion 110 of the first portion 112 that includes the plurality of teeth 114. An end 116 of the second pedicle screw pin 118 also faces the first portion 112. The second pedicle screw pin 188 and the first pedicle screw pin 104 in this implementation are also aligned substantially parallel. Implementations like those in FIG. 11 allow the distractor 102 to be located away from the disc space as the end of the second portion 108 wraps around the pedicle screw. In various implementations, while the first pedicle screw pin 104, second pedicle screw pin 104, the first portion 112 and second portion 108 are all aligned in substantially the same plane, in various implementations, the first and/or the second portions may be angled toward the vertebrae when the distractor 102 is inserted into the pedicle screws. In these implementations, the first and second portions may be further placed out of the way of the disc space as they are located close to the pedicle screws and/or wrap around them. In these implementations, the structure of the first and/or the second portions may be curved in various ways and the shape of the distractor may also be referred to as J-shaped.

Figure 12:
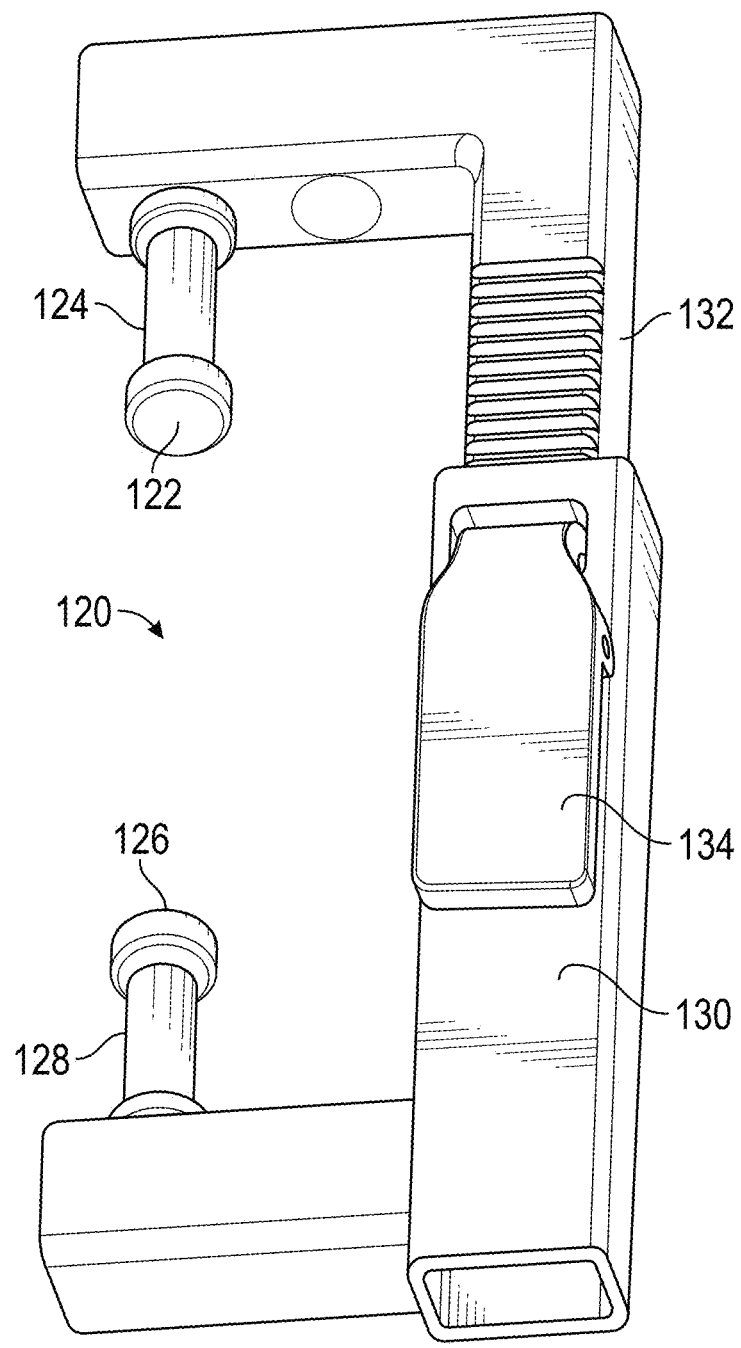
FIG. 12 is a perspective view of a sixth implementation of a distractor device.

Referring to FIG. 12, another implementation of a distractor 120 is illustrated, which may be referred to as a C-shaped distractor. In this implementation, the end 122 of the first pedicle screw pin 124 and the end 126 of the second pedicle screw pin 128 face each other. Also the end 122 of the first pedicle screw pin 124 faces the second portion 130 and the end 126 of the second pedicle screw pin 128 faces the first portion 132. In this implementation, the portion of the distractor 120 that contains the distractor latch 134 is kept out of the way of the disc space by its wrapping around both pedicle screw heads and can be angled toward the vertebrae. Both the C-shaped and J-shaped designs (as well as any of the other distractor implementations disclosed herein) may be used to accomplish ipsilateral provisional distraction.

As the foregoing examples of distractor implementations illustrate, a wide variety of configurations and shapes could be used in various implementations. For example, while the second portions have been illustrated as sleeved and open at the end in most implementations, the distractor 74 illustrated in FIG. 9 has the end of the sleeved second portion 86 closed off so that the second pedicle screw pin 82 can be coupled to the second portion 86. Also, while the various implementations of distractors have used substantially rectangular cross-sections, many other cross-sectional shapes may be utilized in various implementations, such as, by non-limiting example, circular, elliptical, triangular, or any other closed shape. The various distractor implementations may be made of various metals, plastics, or composite materials and may be formed through casting, forming, welding, punching, lathing, molding, injection molding, or any other forming technique adapted to the particular structure to be created and material to be used.

Figure 13:
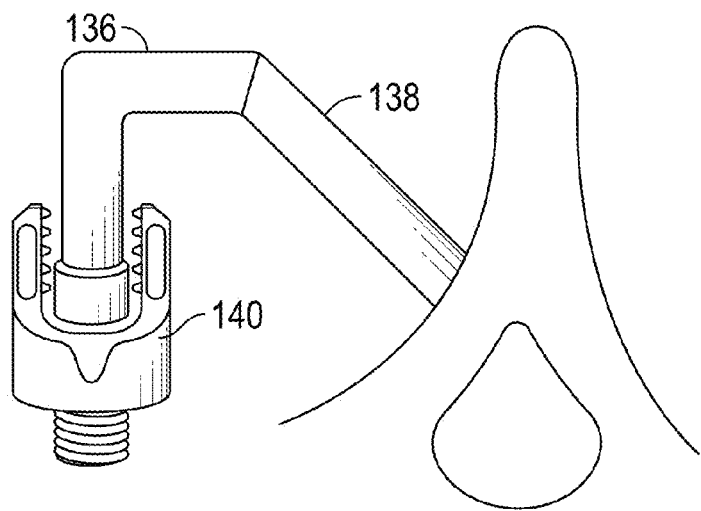
FIG. 13 is a diagram of a medial retractor adjacent to a vertebra.
Figure 14:
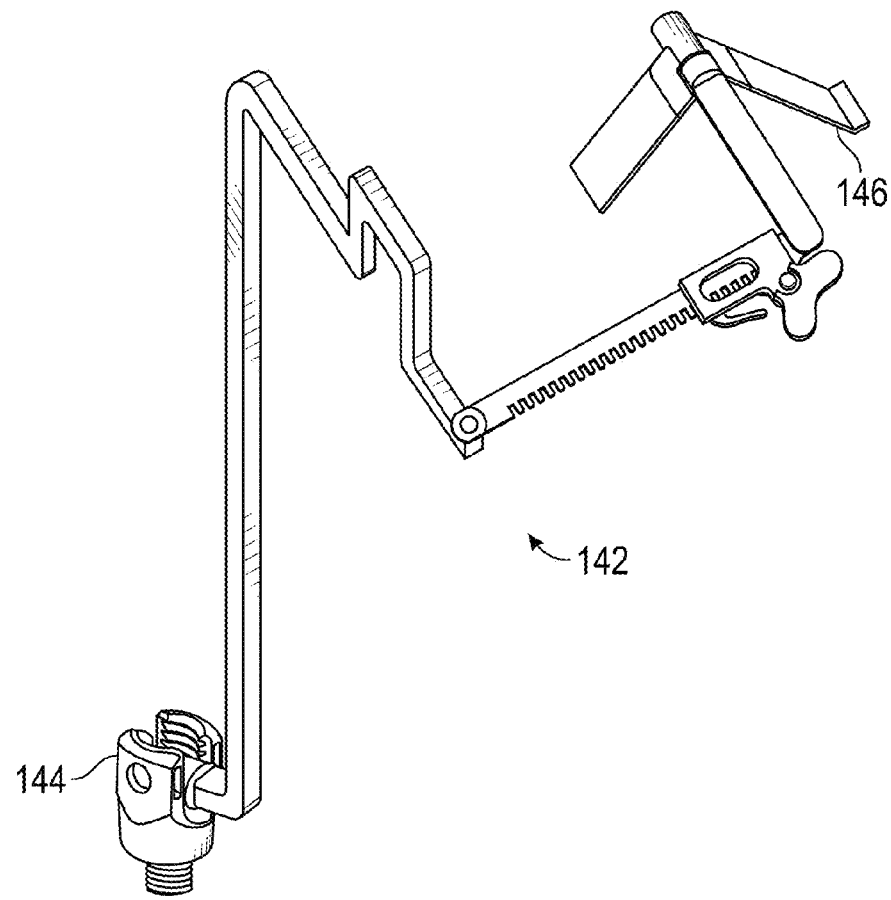
FIG. 14 is a diagram of a medial/lateral retractor implementation coupled to a pedicle screw.

Implementations of MIS TLIF systems like those disclosed herein may also utilize various implementations of medial-lateral retractors. Referring to FIG. 13, a diagram of a cross sectional view of the opening created by a medial-lateral retractor 136 taken perpendicularly to the spreading direction of the retractor blades 138. As can be observed, the medial-lateral retractor 136 is coupled to the pedicle screw 140 on one side, and the remaining blade 138 of the medial-lateral refractor 136 is capable of spreading the opening and angling the opening medially to expose the anatomy sufficiently to allow access to the disc so that a midline decompression of the neural elements can be accomplished. Implementations of medial-lateral retractors disclosed herein may utilize either or both of these aspects, that of being capable of being coupled to the pedicle screw directly or through anchoring with a set screw and the aspect of being able to angulate the medial blade along the vertebra. In addition, various medial-lateral retractor implementations disclosed herein may be coupled directly to any of the distractor implementations disclosed herein through, by non-limiting example, a clip, bracket, latch, screw, pin, or other fastener. Referring to FIG. 14, an implementation of a medial-lateral retractor 142 that incorporates these two aspects, that of coupling to the pedicle screw 144 on the lateral side, and a medial blade 146 that is capable of creating angled medial exposure.

Figure 15:
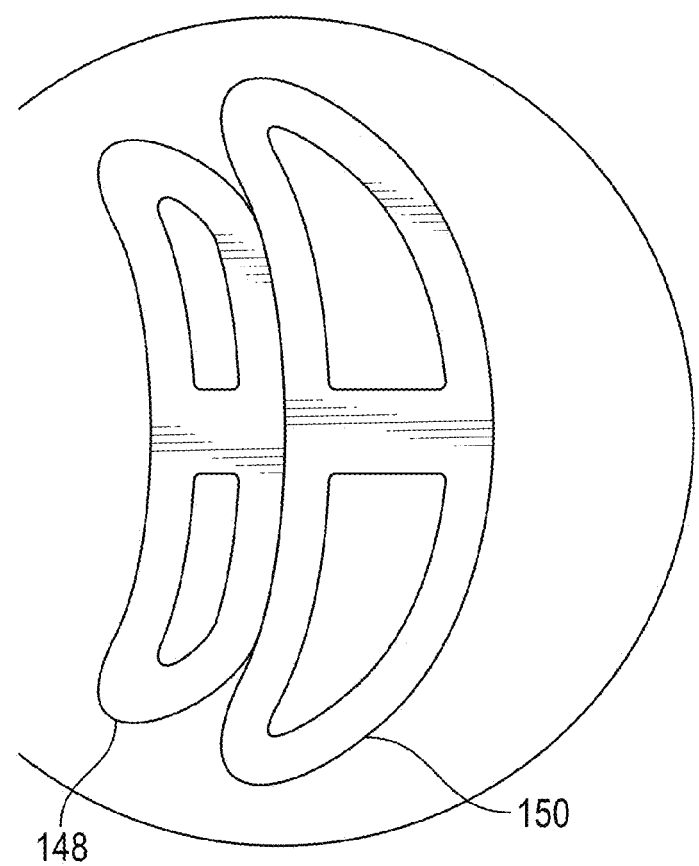
FIG. 15 is a top view of an implementation of nested first and second interbody spacers on top of a vertebra.

Various implementations of MIS TLIF surgical systems and method implementations disclosed herein may utilize various implementations of nested (nestled) interbody spacers. Referring to FIG. 15, a first interbody spacer 148 is shown nested with a second interbody spacer 150 in a top view above the surface of a vertebra. Various conventional interbody spacers can be used in nested configurations, including those marketed under the tradename INTERFUSE by Vertebral Technologies, additional disclosure regarding which is contained in the '839 application. For MIS TLIF surgeries, nesting of conventional spacers marketed under the tradename CRESCENT by Medtronic may be employed to achieve the goals of greater coverage of the interbody devices and increased interbody height. The '839 Application contains disclosure of proof of concept work using such interbody spacers that demonstrate the coverage and interbody height possible with such a configuration. Implementations of nested conventional spacers may ensure lordosis and prevent flat back as well as locking the interbody securely into position without compromising the foramen. In addition, such implementations may reduce the likelihood of migration of the combined nestled spacers.

Figure 16:
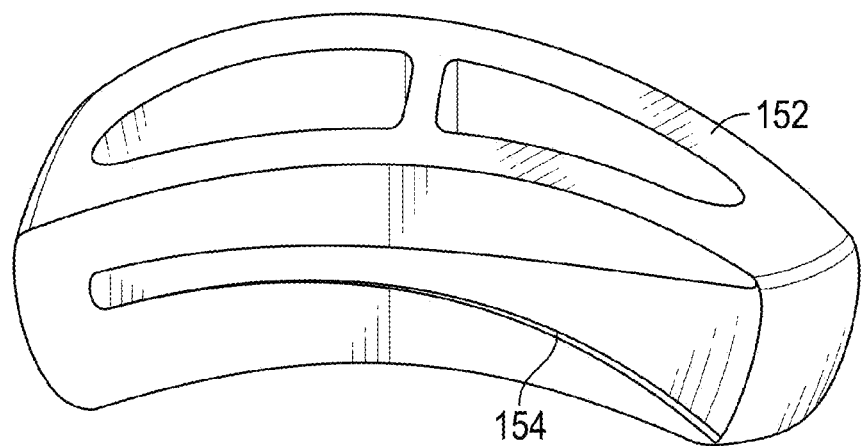
FIG. 16 is a perspective view of an implementation of an interbody spacer showing a tram.
Figure 17:
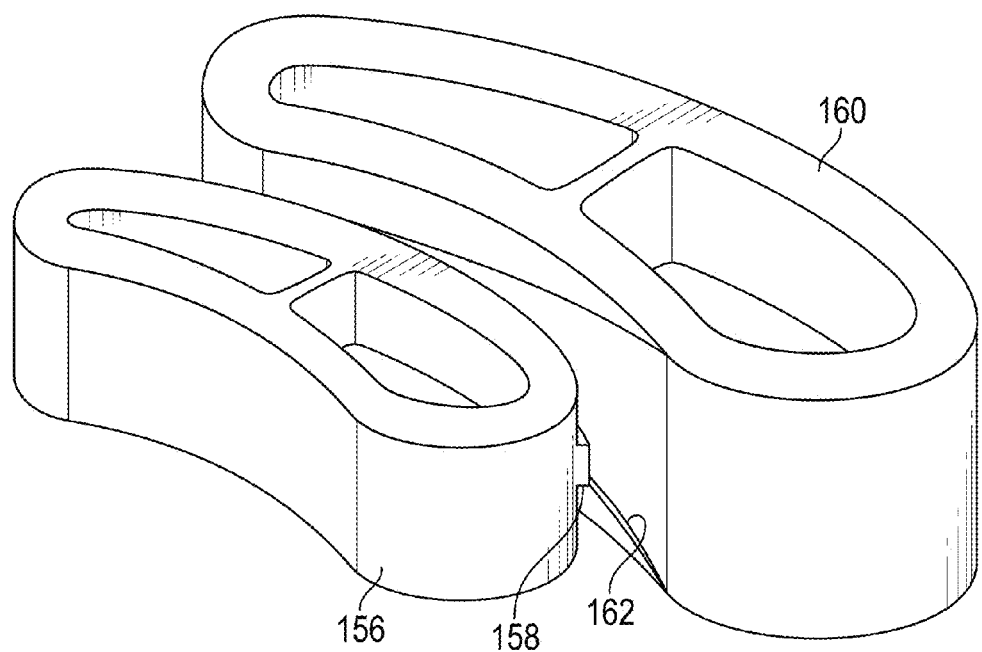
FIG. 17 is a perspective view of implementations of a first interbody spacer and a second interbody spacer.

In situations where nested interbody spacers will be utilized, various implementations of interbody spacers that utilize trams like those disclosed herein may be included to allow them to be sequentially coupled together and inserted into the disc space within the angle allowed during an MIS TLIF surgery (which may be 30 degrees in various situations). Various implementations are detailed in the '839 Application and in this document. Referring to FIG. 16, an interbody spacer 152 with a widened tram 154 to facilitate placement of the second interbody device is illustrated. In some implementations, this tram design may not lock the second interbody device in place to enable removal. In other implementations, the tram design may lock the second interbody device in place to prevent separation of the two interbody devices. Referring to FIG. 17, an implementation of a first interbody spacer 156 containing a pin flange 158 extending from at least a portion of the side of the first interbody spacer 156 is illustrated adjacent to a second interbody spacer 160 that includes a tram 162 in at least a portion of a side of the second interbody spacer 160. Various implementations may have the pin flange 158 and the tram 162 extend along a majority or all of the sides of the first interbody spacer 156 and second interbody spacer 160. The pin flange 158 is sized to slide into the tram 162 and slidably couple to the first interbody spacer 156 and the second interbody spacer 160 together. During use, the surgeon would first insert the second interbody spacer 160 in between the vertebrae, and then would insert the pin flange 158 of the first interbody spacer 156 into the tram 162 and slide the first interbody spacer 156 into the space between the two vertebrae. If the two interbody spacers needed to be removed, the removal process would be the opposite of the insertion process.

Those of skill in the art will readily appreciate that a set of various spacers with trams can be constructed for various desired spacer sizes. Also, any number of interbody spacers could be nested in various configurations, where one or more interbody spacers could have both a pin flange and a tram to enable it to slidably couple two other interbody spacers together.

Figure 18:
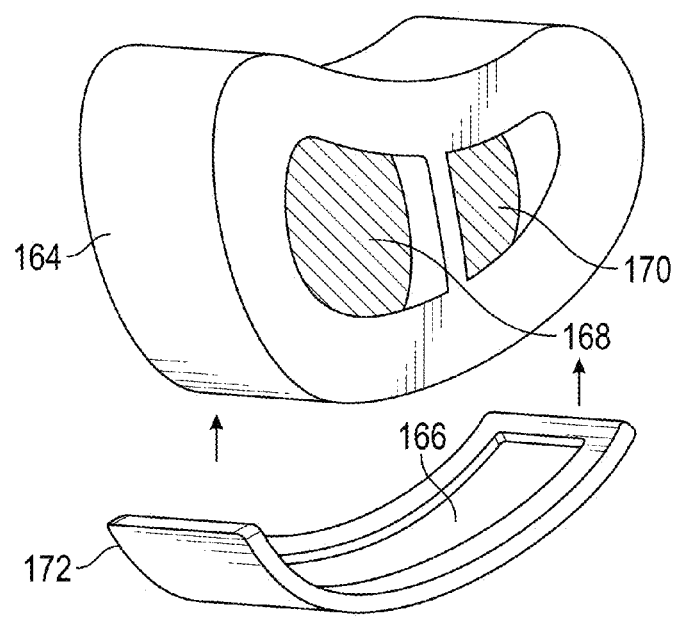
FIG. 18 is a perspective view of an interbody spacer showing a cover.
Figure 19:
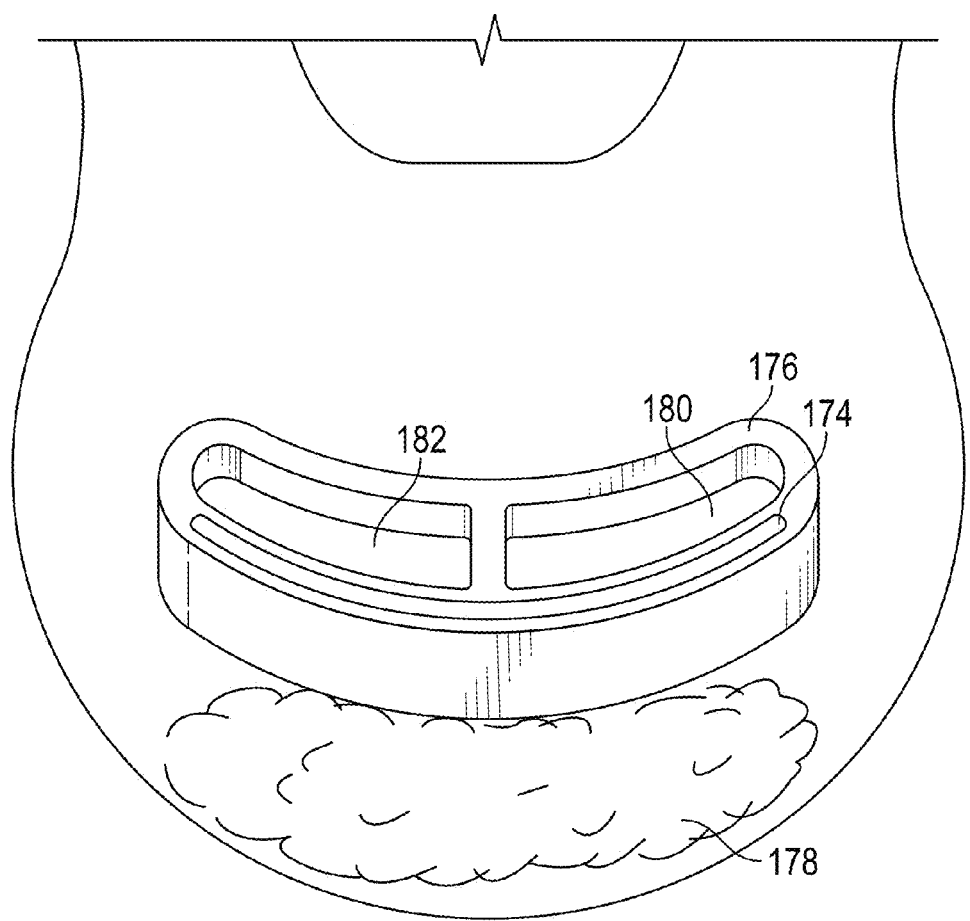
FIG. 19 is a top perspective view of an interbody spacer implementation adjacent to allograft material on a vertebra.

Referring to FIGS. 18 and 19, the various interbody spacer implementations (particularly second interbody spacers) could be modified to contain a compartment for the inclusion of rh-BMP-2. Referring to FIG. 18, an implementation of an interbody spacer 164 containing a third chamber 166 on the anterior aspect of interbody spacer 164 configured to hold a sponge containing rh-BMP-2 is illustrated. As illustrated, the third chamber 166 is formed after the autograft or allograft is placed within the existing two chambers 168, 170 of the interbody spacer 164 by placing a sponge containing rh-BMP-2 on the anterior aspect of the device and a cover 172 being placed over it. In particular implementations, the cover 172 functions as a screen supporting the sponge and places the rh-BMP-2 in the vicinity of the allograft or autograft but away from the neural elements. In particular implementations, about 1.05 mg of rh-BMP-2 may be included. In other implementations, referring to FIG. 18, the cover may contain an opening on one or both of its longest dimensions that leaves an opening 174 on one or both sides of the interbody spacer 176. In these implementations, the cover would not function as a screen. As illustrated in FIG. 19, the allograft/autograft material 178 can be placed in between the vertebrae first, followed by the second interbody spacer 176 with the opening(s) that permit the sponge containing rh-BMP-2 to be made available to the bone. Allograft/autograft material can also be placed in the other two chambers 180, 182.

In implementations of interbody spacers utilizing a third chamber, the sponge size that is selected may be extra-extra small among conventional sponge sizes. The use of the third chamber may prevent issues noted in conventional surgeries due to migration of the small sponge within the existing chambers of conventional large spacers and from compression of the sponge. In addition, the use of the third chamber increases the surgeon's ability to prevent or limit contact of the rh-BMP-2 with the neural elements which may result in minimization of any delayed complications resulting from use of the rh-BMP-2.

Referring now to FIGS. 24-27, a medial lateral refractor system implementations 202 is illustrated that may be used in MIS TLIF procedures like those disclosed in this document. The medial lateral refractor system 202 includes a rostral retractor blade 204 and a caudal refractor blade 206 configured to move away from, and towards, each other along a linear direction and also configured to rotate with respect to one another along a plane. A first rotator 208 and second rotator 210 allow the rotation of the rostral retractor blade 204 and caudal retractor blade 206, respectively, and a first rotator lock 212 and second rotator lock 214 are configure to lock a desired rotation of the rostral retractor blade 204 and caudal retractor blade 206, respectively, in place. A first handle 216 and second handle 218, each of which can be adjusted to different positions, provide a mechanism for a user to provide pressure to bring the two handles closer together and thus rotate the rostral retractor blade 204 and the caudal retractor blade 206 away from one another.

The first rotator 208 is rotatably coupled to a base member 224, and the second rotator 210 is rotatably coupled to a second rotator coupler 220 which in turn is coupled to the base member through a first sleeve 222. Couplers 226 allow the base member 224 to be coupled to external elements. Grooves 228 of the base member 224 work in concert with a retractor blade width adjuster 230, which in the implementation shown is a turnscrew 232, and a releasable lock 234 which selectively locks the sleeve 222 at a desired location relative to the base member 224. Thus, by turning the turnscrew 232 in a first rotation the sleeve 222 is moved along a first direction relative to the base member 224 and, in turn, the rostral retractor blade 204 and caudal retractor blade 206 are moved away from each other along a direction substantially parallel with the direction of movement of the sleeve 222 relative to the base member 224. When the turnscrew 232 is turned in the opposite rotation the rostral retractor blade 204 and caudal retractor blade 206 are drawn towards one another along the same direction. In implementations the releasable lock 234 is configured such that movement of the rostral refractor blade 204 towards the caudal retractor blade 206 along the direction, by virtue of movement of the sleeve 222 relative to the base member 224, is prevented until the releasable lock 234 is manually released by a user, but movement of the rostral retractor blade 204 away from the caudal refractor blade 206 along the same direction is not prevented by the releasable lock 234.

Figure 27:
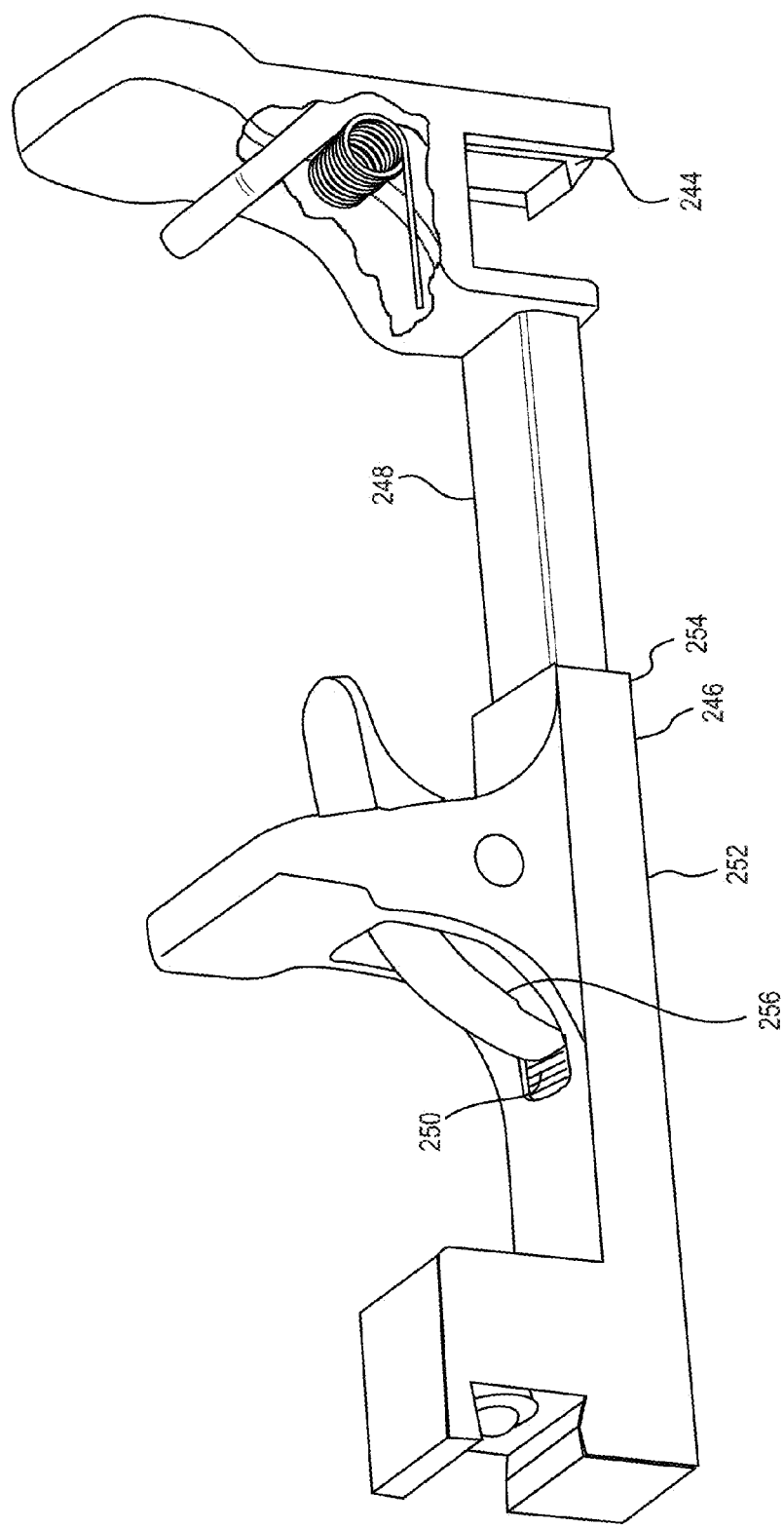
FIG. 27 is a top-side perspective view of portions of the medial lateral retractor system of FIG. 24.

In implementations the medial lateral retractor system 202 includes a first medial lateral retractor arm (retractor arm) 236 and a second medial lateral retractor arm (refractor arm) 240. In implementations the first medial lateral retractor arm 236 includes fingers 238 and the second medial lateral retractor arm 240 includes fingers 242, though, in particular implementations, the fingers 238 and 242 may be omitted. A base member coupler 244 couples the retractor arms 236, 240 to the base member 224. The base member coupler 244 is not couplable to the location of the base member 224 where it is coupled in FIGS. 24-25 until the sleeve 222 is moved along the base member 224 a specified distance to distance the rostral retractor blade 204 from the caudal retractor blade 206. In particular implementations, the base member coupler 244 may be not be engaged between the couplers 226 adjacent to the sleeve 222 (top down engagement), but may be engaged directly to either of the couplers 226. In specific implementations, the base member coupler 244 may be engaged to the uppermost coupler 226 shown in FIG. 24 permitting the base member coupler 244 to be coupled at the end rather than between the couplers 226 (end coupling). To accomplish this, the base member coupler 244 is rotated 90 degrees from the orientation shown in FIG. 24 to allow it to couple to the upper most coupler 226. As can be seen in FIG. 27, in implementations the base member coupler 244 includes a clip member which clips around the base member 224 and is biased towards a closed (clipped-on) configuration through the use of a bias spring, but the bias may be overcome through applying pressure to a tab member to release the clip member and allow the base member coupler 244 to be removed from the base member 224.

A lateral adjuster 246 has a first member 248 that couples to the base member coupler 244 and a second member 252 which includes a sleeve 254 slidably coupled to the first member 248. A releasable lock 256 is configured to interact with grooves 250 of the first member 248 to selectively allow and disallow sliding of the first member 248 relative to the second member 252. The lateral adjuster 246 allows the first medial lateral retractor arm 236 and second medial lateral retractor arm 240 to be jointly moved in a direction that is substantially perpendicular to the direction of movement of the rostral retractor blade 204 and caudal retractor blade 206.

As illustrated, a retractor arm interconnect 264 couples the first medial lateral retractor arm 236 to the second medial lateral retractor arm 240. A second interconnect section 270 includes a sleeve 272 which is slidably coupled to a first interconnect section 266, and a retractor arm width adjuster 274 includes a turnscrew 276 which interacts with grooves 268 of the first interconnect section 266 to slide the sleeve 272 relative to the first interconnect section 266. A releasable lock 278 operates together with the grooves 268 similarly to the releasable lock 234 relative to the grooves 228 to selectively allow and disallow movement of the sleeve 254 relative to the first interconnect section 266.

Movement of the second interconnect section 270 relative to the first interconnect section 266 functions to move the second medial lateral refractor arm 240 relative to the first medial lateral retractor arm 236 along a direction that is substantially perpendicular to the direction of movement of the rostral retractor blade 204 relative to the caudal refractor blade 206. In particular implementations, the releasable lock 278 disallows movement of the second medial lateral retractor arm 240 towards the first medial lateral retractor arm 236 until a user manually operates to release the releasable lock 278 but the releasable lock 278 does not prevent movement of the second medial lateral retractor arm 240 away from the first medial lateral retractor arm 236 by rotation of the retractor arm width adjuster 274.

A retractor arm rotation adjuster 258 rotates the second medial lateral retractor arm 240 about an axle 262 which couples the second medial lateral retractor arm 240 to the second interconnect section. In implementations the retractor arm rotation adjuster includes a turnscrew 260. The retractor arm rotation adjuster 258 allows rotation of the first medial lateral retractor arm 236 and second medial lateral retractor arm 240 towards and away from one another along a plane that is substantially perpendicular to the plane along which the rostral retractor blade 204 and caudal retractor blade 206 may be rotated towards and away from one another by use of the first rotator 208 and second rotator 210.

Figure 24:
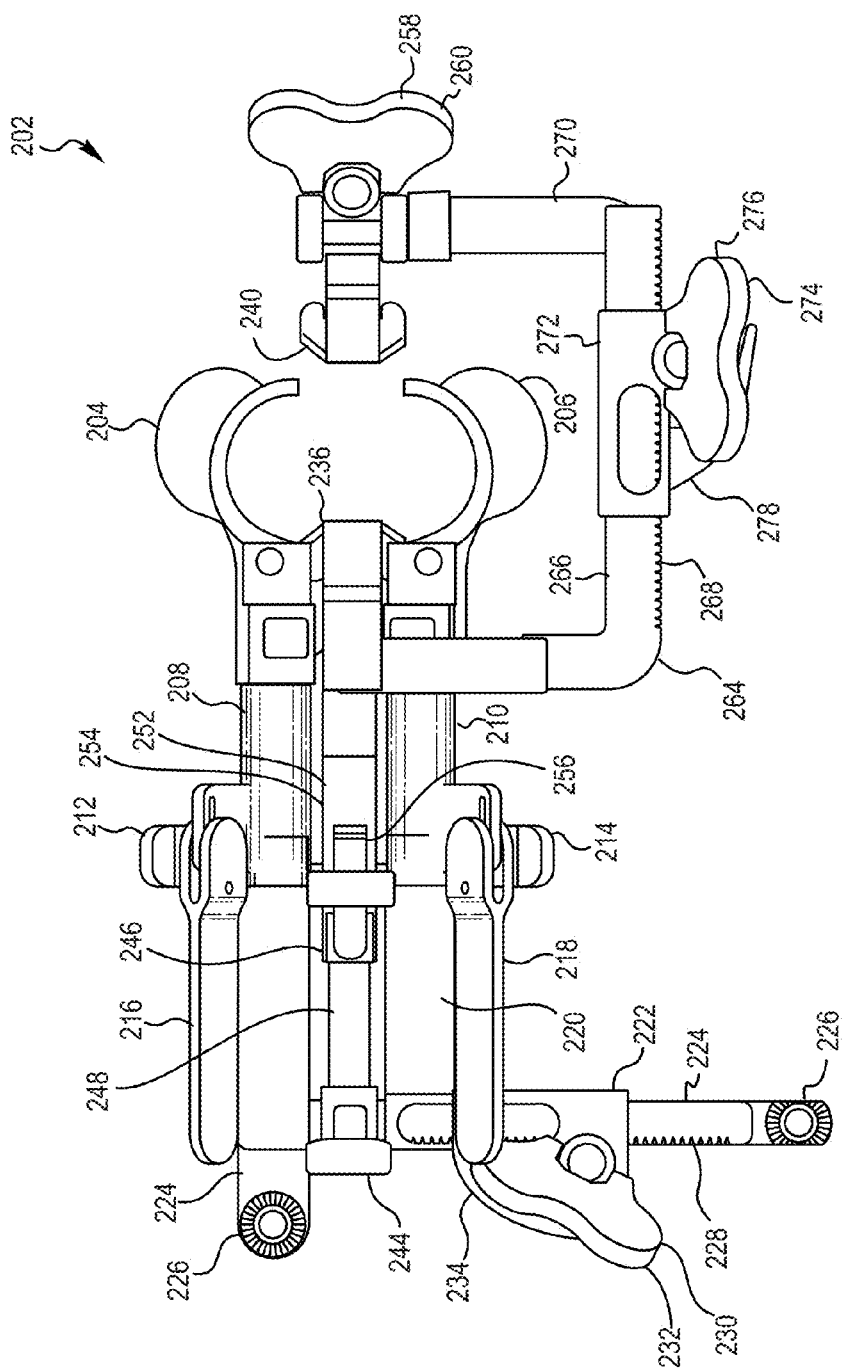
FIG. 24 is a top view of an implementation of a medial lateral retractor system.
Figure 25:
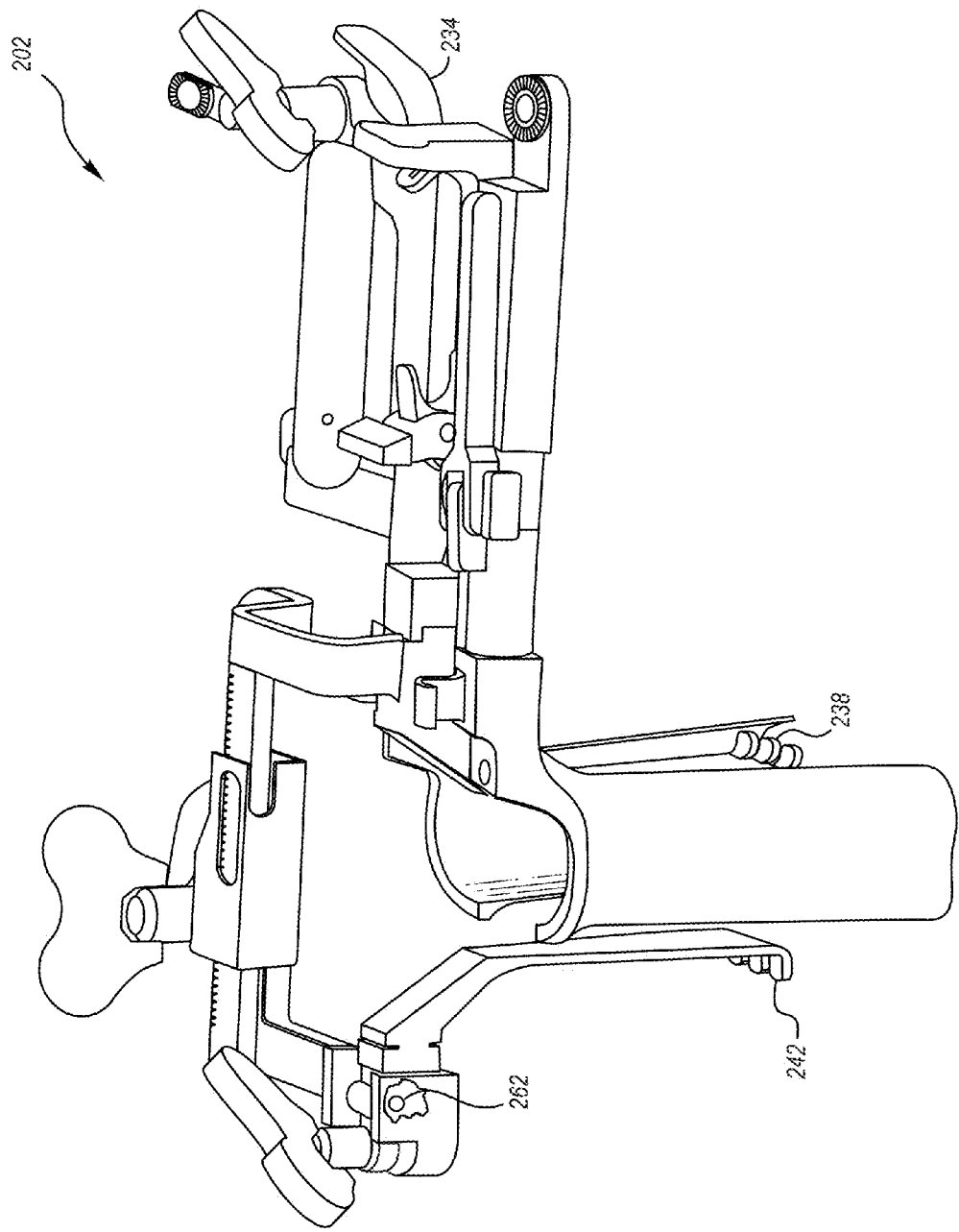
FIG. 25 is a top-side perspective view of the medial lateral retractor system of FIG. 24.
Figure 26:
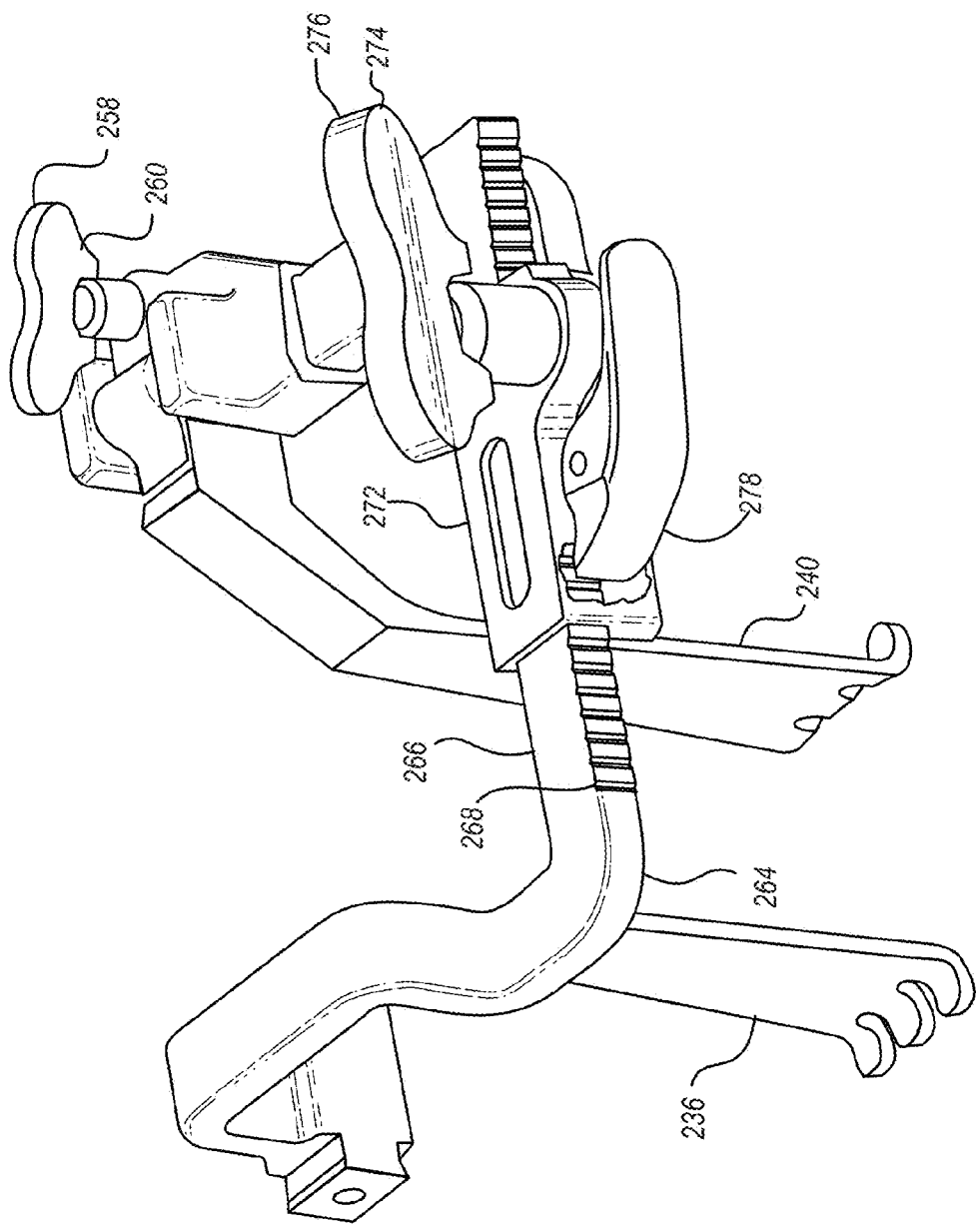
FIG. 26 is a top-side perspective view of portions of the medial lateral retractor system of FIG. 24.

Implementations of a medial lateral retractor system include only the elements shown in FIGS. 26 and 27, while other implementations of a medial lateral retractor system 202 include all of the elements shown in FIGS. 24-25. In implementations, as shown in FIG. 24, the retractor arm interconnect 264 is configured such that it does not interfere with the line of sight, looking downwards, between the rostral retractor blade 204 and caudal retractor blade 206. In implementations this is accomplished by fashioning the retractor arm interconnect 264 to have a U-shape.

The operation of a medial lateral retractor system 202 is such that, during an operation, the rostral retractor blade 204 and caudal retractor blade 206 may first be distanced from one another and/or rotated away from each other to push muscle, skin and/or other tissue or items out of the way to allow a surgical operational procedure to be performed therebetween. After the rostral retractor blade 204 and caudal retractor blade 206 have been distanced from one another a specified amount through use of the retractor blade width adjuster 230, the sleeve 222 will have moved a sufficient distance to allow the base member coupler 244 to couple to the base member 224 at the location shown in FIGS. 24-25. In this manner the first medial lateral retractor arm 236 and second medial lateral retractor arm 240 are coupled to the base member only after the rostral retractor blade 204 and caudal retractor blade 206 have been separated from one another a specified distance, and thus the elements that allow movement, positioning and use of the rostral retractor blade 204 and caudal retractor blade 206, and the elements that allow movement, positioning and use of the first medial lateral retractor arm 236 and second medial lateral retractor arm 240, are generally included in two separate units. In other implementations the base member coupler 244 could be permanently coupled to the base member 224 or some other element.

The movement, positioning, and use of the first medial lateral retractor arm 236 and second medial lateral refractor arm 240 may thus assist in separating the muscle, skin, tissue, and/or other element(s) that are being separated by the rostral retractor blade 204 and caudal retractor blade 206 during a surgical operation. The first medial lateral retractor arm 236 and second medial lateral retractor arm 240 may allow the muscle, skin, tissue and/or other element(s) to be separated to a greater extent and/or along more directions than is possible through the use of only the rostral retractor blade 204 and caudal retractor blade 206, thus making a surgical operational procedure between the blades 204, 206 and retractor arms 236, 240, easier, quicker, and/or more easily viewed by a person performing the operation, or another person, or a camera or recording device, and/or the like.

Before and during a surgical procedure the rostral retractor blade 204, caudal retractor blade 206, first medial lateral retractor arm 236 and second medial lateral retractor arm 240 may be adjusted, distanced, brought closer together, shifted in unison or separately, rotated, and the like, in a variety of ways, as can be perceived from the description and drawings, to separate and or move muscle, tissue, skin and/or other elements, as desired, to facilitate the surgical procedure and/or to make it more quick, more easily performed, more easily viewed, and/or the like while being performed in a minimally invasive manner.

After a surgical procedure, or a portion thereof, is completed, a user may adjust the first medial lateral retractor arm 236 and/or the second medial lateral retractor arm 240 such as, by non-limiting example, by rotating the second medial lateral retractor arm 240 closer towards the first medial lateral retractor arm 236 through the use of the retractor arm rotation adjuster 258, moving the second medial lateral retractor arm 240 closer to the first medial lateral retractor arm 236 through the use of the retractor arm width adjuster 274, and/or moving the first medial lateral retractor arm 236 and second medial lateral retractor arm 236 closer to or further from the base member 224, in unison, using the lateral adjuster 246, to facilitate and/or make more easier the removal of the first medial lateral retractor arm 236 and second medial lateral refractor arm 240 from the operation by removal of the base member coupler 244 from the base member 224. The rostral retractor blade 204 and caudal retractor blade 206 may similarly be removed from the operation thereafter.

In implementations the medial lateral retractor system 202 may be made, or substantially made, of one or more radiolucent materials.

As can be seen in FIGS. 25-27, in implementations the first medial lateral retractor arm 236 is removably coupled to the second member 252.

A method of using a medial lateral refractor system 202 may include movably coupling a first medial lateral refractor arm 236 to a second medial lateral retractor arm 240, coupling a base member coupler 244 to one of the first medial lateral retractor arm 236 and the second medial lateral retractor arm 240, and coupling the base member coupler 244 to a base member 224 to which a caudal retractor blade 206 and rostral retractor blade 204 are coupled, at a location made available only by distancing the caudal retractor blade 206 from the rostral retractor blade 204 a predetermined amount, wherein the first medial lateral retractor arm 236 is configured to move away from the second medial lateral retractor arm 240 in a direction that is substantially perpendicular to a direction of movement of the rostral retractor blade 204 away from the caudal retractor blade 206 when the base member coupler 244 is coupled to the base member 224.

In places where the description above refers to particular implementations of retractors, distractor devices, interbody spacers and implementing components, sub-components, methods and sub-methods, it should be readily apparent that a number of modifications may be made without departing from the spirit thereof and that these implementations, implementing components, sub-components, methods and sub-methods may be applied to other retractors, distractor devices, interbody spacers and implementing components.

What is claimed is:

1. A medial lateral retractor system, comprising:
   a first medial lateral retractor arm;
   a second medial lateral retractor arm movably coupled to the first medial lateral retractor arm;
   a base member coupler coupled to one of the first medial lateral retractor arm and the second medial lateral retractor arm and configured to couple to a base member to which a rostral retractor blade and caudal retractor blade are coupled; and
   a lateral adjuster coupled between the base member coupler and one of the first medial lateral retractor arm and the second medial lateral retractor arm, the lateral adjuster configured to jointly move the first medial lateral retractor arm and the second medial lateral retractor arm in a direction substantially perpendicular to a direction of movement of the rostral retractor blade relative to the caudal retractor blade when the base member coupler is coupled to the base member;
   wherein the first medial lateral retractor arm is also configured to move relative to the second medial lateral retractor arm in the direction that is substantially perpendicular to the direction of movement of the rostral retractor blade relative to the caudal retractor blade when the base member coupler is coupled to the base member.

2. The system of claim 1, wherein the medial lateral retractor further comprises the base member, the rostral retractor blade and the caudal retractor blade, and wherein the base member is coupled to the base member coupler.

3. The system of claim 1, wherein the medial lateral retractor system is substantially comprised of a radiolucent material.

4. The system of claim 1, wherein the first medial lateral retractor arm and second medial retractor arm each comprise a plurality of finger members.

5. The system of claim 1, wherein the lateral adjuster comprises a first member slidably engaging a second member and a releasable lock coupled to one of the first member and second member and configured to selectively prevent and allow sliding of the first member relative to the second member.

6. The system of claim 1, further comprising a retractor arm width adjuster coupled to one of the first medial lateral retractor arm and the second medial lateral retractor arm and configured to adjust a distance between the first medial lateral retractor arm and second medial lateral retractor arm along a direction substantially perpendicular to a direction of movement of the rostral retractor blade relative to the caudal retractor blade when the base member coupler is coupled to the base member.

7. The system of claim 6, further comprising a first interconnect section coupled to the first medial lateral retractor arm, a second interconnect section coupled to the second medial lateral retractor arm and slidably engaging the first interconnect section, and a releasable lock coupled to one of the first interconnect section and second interconnect section and configured to selectively prevent and allow sliding of the first interconnect section relative to the second interconnect section, and wherein the retractor arm width adjuster is configured to slide the first interconnect section relative to the second interconnect section.

8. The system of claim 1, further comprising a retractor arm rotation adjuster coupled to one of the first medial lateral retractor arm and the second medial lateral retractor arm and configured to rotate the first medial lateral retractor arm relative to the second medial lateral retractor arm in a plane that is substantially perpendicular to a plane of rotation of the rostral retractor blade relative to the caudal retractor blade when the base member is coupled to the base member.

9. The system of claim 8, wherein the retractor arm rotation adjuster is configured to rotate one of the first medial lateral retractor arm and second medial retractor arm about an axle.

10. The system of claim 1, wherein the first medial lateral retractor arm and second medial lateral retractor arm are coupled together only with elements that do not obstruct a downwards-looking field of view between the rostral retractor blade and caudal retractor blade.

11. The system of claim 10, wherein the first medial lateral retractor arm and second medial lateral retractor arm are coupled together with a u-shaped element.

12. The system of claim 1 wherein the base member coupler is coupled to the base member at a location only made available upon distancing the rostral retractor blade from the caudal retractor blade a predetermined amount.

13. A medial lateral retractor system, comprising:
   a first medial lateral retractor arm;
   a second medial lateral retractor arm movably coupled to the first medial lateral retractor arm;
   a base member coupler coupled to one of the first medial lateral retractor arm and the second medial lateral retractor arm;
   a base member coupled to the base member coupler;
   a rostral retractor blade coupled to the base member;
   a caudal retractor blade coupled to the base member; and
   a retractor arm rotation adjuster coupled to one of the first medial lateral retractor arm and the second medial lateral retractor arm and configured to rotate the first medial lateral retractor arm relative to the second medial lateral retractor arm in a plane that is substantially perpendicular to a plane of rotation of the rostral retractor blade relative to the caudal retractor blade when the base member coupler is coupled to the base member;
   wherein the first medial lateral retractor arm is configured to move away from the second medial lateral retractor arm in a direction that is substantially perpendicular to a direction of movement of the rostral retractor blade away from the caudal retractor blade when the base member coupler is coupled to the base member.

14. The system of claim 13, wherein the base member coupler is coupled to the base member at a location only made available upon distancing the rostral retractor blade from the caudal retractor blade a predetermined amount.

15. A method of using a medial lateral retractor system, comprising:
   movably coupling a first medial lateral retractor arm to a second medial lateral retractor arm;
   coupling a base member coupler to one of the first medial lateral retractor arm and the second medial lateral retractor arm; and
   coupling the base member coupler to a base member, to which a caudal retractor blade and rostral retractor blade are coupled, at a location made available only by distancing the caudal retractor blade from the rostral retractor blade a predetermined amount;
   wherein the first medial lateral retractor arm is configured to move away from the second medial lateral retractor arm in a direction that is substantially perpendicular to a direction of movement of the rostral retractor blade away from the caudal retractor blade when the base member coupler is coupled to the base member.

* * * * *